United States Patent
Medoff et al.

(10) Patent No.: US 10,364,412 B2
(45) Date of Patent: Jul. 30, 2019

(54) APPARATUS FOR PROVIDING LARGE AMOUNTS OF GAS TO A FERMENTATION BROTH

(71) Applicant: XYLECO, INC., Wakefield, MA (US)

(72) Inventors: Marshall Medoff, Wakefield, MA (US); Thomas Craig Masterman, Rockport, MA (US); Robert Paradis, Burlington, MA (US); Aiichiro Yoshida, Canton, MA (US); Karen Heinze, Medford, MA (US)

(73) Assignee: XYLECO, INC., Wakefield, MA (US)

( * ) Notice: Subject to any disclaimer, the term of this patent is extended or adjusted under 35 U.S.C. 154(b) by 0 days.

(21) Appl. No.: 15/112,909

(22) PCT Filed: Jul. 6, 2016

(86) PCT No.: PCT/US2016/041038
§ 371 (c)(1),
(2) Date: Jul. 20, 2016

(87) PCT Pub. No.: WO2017/007788
PCT Pub. Date: Jan. 12, 2017

(65) Prior Publication Data
US 2018/0105786 A1    Apr. 19, 2018

Related U.S. Application Data

(60) Provisional application No. 62/189,316, filed on Jul. 7, 2015.

(51) Int. Cl.
*C12M 1/00*    (2006.01)
*C12M 1/04*    (2006.01)
*C12M 1/36*    (2006.01)

(52) U.S. Cl.
CPC .............. *C12M 29/06* (2013.01); *C12M 1/04* (2013.01); *C12M 1/36* (2013.01)

(58) Field of Classification Search
CPC ...... C12M 29/06; C12M 29/24; C12M 27/00; C12M 41/32; C12M 41/34; C12M 21/12; C12M 41/48
See application file for complete search history.

(56) References Cited

U.S. PATENT DOCUMENTS 3,619,369 A    11/1971  Onishi et al.
3,968,035 A *   7/1976  Howe ................... C02F 3/1284
                                                    210/621
(Continued)

FOREIGN PATENT DOCUMENTS

CN    85100522 A    7/1986
EP    2695861 A1    2/2014
(Continued)

OTHER PUBLICATIONS

International Search Report and Written Opinon for PCT application No. PCT/US16/41038 dated Sep. 29, 2016.
(Continued)

*Primary Examiner* — Gautam Prakash
(74) *Attorney, Agent, or Firm* — Lando & Anastasi, LLP

(57) ABSTRACT

According to various aspects and embodiments, a system and method for aerobic fermentation of an aqueous sugar solution is provided. The system includes a vessel, at least one air diffuser in fluid communication with an interior of the vessel, and at least one blower that is configured to deliver air to the at least one air diffuser.

18 Claims, 16 Drawing Sheets

(56) References Cited

U.S. PATENT DOCUMENTS

| | | | |
|---|---|---|---|
| 4,426,450 A | | 1/1984 | Donofrio |
| 5,198,362 A | * | 3/1993 | Forsyth et al. ..... B01F 3/04531 435/243 |
| 5,656,155 A | | 8/1997 | Norcross et al. |
| 7,374,675 B2 | * | 5/2008 | Koopnnans et al. ......................... C02F 3/1284 210/220 |
| 2002/0138454 A1 | * | 9/2002 | Gruenberg et al. .... C12M 41/48 706/7 |
| 2006/0270036 A1 | | 11/2006 | Goodwin et al. |
| 2011/0117538 A1 | | 5/2011 | Niazi |
| 2012/0202282 A1 | * | 8/2012 | Hinkens et al. ....... C12M 21/02 435/292.1 |
| 2013/0189763 A1 | * | 7/2013 | Dalla-Betta et al. .. C12M 29/02 435/252.1 |
| 2013/0323714 A1 | | 12/2013 | Cheng et al. |
| 2014/0004570 A1 | | 1/2014 | Medoff et al. |
| 2015/0071575 A1 | | 3/2015 | Galliher et al. |
| 2015/0136136 A1 | * | 5/2015 | Fleming et al. ....... A61B 5/087 128/204.23 |

FOREIGN PATENT DOCUMENTS

| | | |
|---|---|---|
| WO | 0144119 A1 | 6/2001 |
| WO | 2011022840 A1 | 3/2011 |
| WO | 2013096693 A1 | 6/2013 |

OTHER PUBLICATIONS

Kaufman et al., "Fermentation: Critical Process Phenomena and New Technology Developments That Affect Yield and Productivity" Pharmaceutical Engineering, vol. 17, No. 5, 1997, pp. 1-2. Retrieved from Internet <http://canaley.com/wp-content/uploads/2012/01/R191a.pdf>.

Riek et al., "An automated home-built low-cost fermenter suitable for large-scale bacterial expression of proteins in *Escerichia coli*" BioTechniques, vol. 45, No. 2, pp. 187-189. Retrieved from the Internet <http://www.biotechniques.com/multimedia/archive/00001/BTN_A_000112830_O_1890a.pdf>.

Fermentaton Technology, "Rheology of Fermentation Broth" Feb. 12, 2008, Retrieved from the Internet <http://fermentationtechnology.blogspot.com/2008/02/rheology-of-fermentation-broth.html>.

Alvarez et al., "Automation strategies for dissolved oxygen control in real activated-sludge plants", Control & Automation (MED), 2012 20th Mediterranean Conference on, IEEE, Jul. 2012, pp. 770-775.

Extended European Search Report from European Application No. 16821891.5 dated Feb. 25, 2019.

Office Action from Eurasian Application No. 201791932 dated Apr. 1, 2019.

Yoo et al., "Development of thin-film photo-bioreactor and its application to outdoor culture of microalgae", Bioprocess and Biosystems Engineering, vol. 36, No. 6, Jun. 2013, pp. 729-736.

* cited by examiner

APPARATUS FOR PROVIDING LARGE AMOUNTS OF GAS TO A FERMENTATION BROTH

CROSS-REFERENCE TO RELATED APPLICATIONS

This application is the U.S. National Phase Application under 35 U.S.C. § 371 of International (PCT) Patent Application Serial No. PCT/US2016/041038, filed Jul. 6, 2016, which claims priority under 35 U.S.C. § 119(e) to U.S. Provisional Patent Application Serial No. 62/189,316 filed Jul. 7, 2015, the disclosures of which are hereby incorporated by reference in their entireties.

BACKGROUND

Technical Field

The technical field relates generally to methods and systems for producing a fermentation product from a cellulosic or lignocellulosic biomass.

Background Discussion

Lignocellulosic biomass, such as agricultural residues, woody biomass, municipal waste, oilseeds/cakes, and seaweeds function as renewable feedstock that may be used for manufacturing bioproducts, such as biofuels and biochemicals. Many of these biomass materials are attractive in that they are abundant, renewable, domestically produced, and may not compete with food industry uses. Currently, many of these materials are used as animal feed, biocompost material, burned in a cogeneration facility or landfilled. Lignocellulosic biomass is recalcitrant to degradation as the plant cell walls have a structure that is rigid and compact. Saccharides from renewable biomass sources could become the basis of chemical and fuels industries by replacing, supplementing or substituting petroleum and other fossil feedstocks.

Fermentable sugar solutions may be produced from the polysaccharide components of the feedstock, such as cellulose and hemicelluloses. In order to produce sugar from lignocellulosic feedstocks, it is first necessary to break them down into their composite sugar molecules. This can be accomplished by physical and/or chemical pretreatment. Examples of chemical pretreatment are acid pretreatment (see U.S. Pat. No. 4,461,648) or alkali pretreatment, such as Ammonia Fiber Explosion (AFEX) pretreatment. Acid pretreatment hydrolyzes most of the hemicellulose, but there is little conversion of the cellulose to glucose. On the other hand, alkali pretreatment methods may or may not hydrolyze hemicellulose, although in either case the base reacts with acidic groups present on the hemicellulose to open up the surface of the substrate. After pretreatment with acid or alkali, the cellulose may then be hydrolyzed to glucose by cellulase enzymes or by further chemical treatment. Glucose can then be fermented to fuels including, but not limited to, ethanol, butanol, or other chemicals, examples of which include sugar alcohols and organic acids.

SUMMARY

Aspects and embodiments are directed to systems and methods for fermenting and to delivery of gases, such as air to fermentation broths. For example, systems and methods are described that provide large amounts of a gas, such as air, that can be used for aerobic fermentation. The gas, such as air, can be provided at a fraction of the cost of high pressure compressed gas, such as those routinely used in various fermentations. For example, relatively low pressure air, e.g., less than 25 psig, can be provided for the production of proteins, such as enzymes, e.g., cellulases. In addition to providing a gas, such as air, at a fraction of the cost of high pressure gas systems, the systems and methods described herein have lower capital costs and lower maintenance in comparison to typical high pressure systems.

In accordance with one or more embodiments, a system for delivering a gas to an aqueous liquid, such as a system for aerobic fermentation of an aqueous liquid, is provided. The system may comprise: a vessel, at least one sparge tube in fluid communication with an interior of the vessel, and at least one blower configured to deliver a gas to the at least one sparge tube.

According to some embodiments, the at least one sparge tube is constructed from a porous metal. According to at least one embodiment, the at least one sparge tube is positioned in a lower portion of the vessel.

In accordance with certain embodiments, the vessel has an aspect ratio of 2:1.

According to another embodiment, the system further comprises at least one filter configured to filter air delivered from the at least one blower to the at least one sparge tube. According to another embodiment, the system further comprises a heat exchanger having an inlet in fluid communication with an outlet of the blower and an outlet in fluid communication with the at least one filter. According to yet another embodiment, the system further comprises flexible conduit material coupled to the at least one filter and the heat exchanger. According to another embodiment, the system includes a plurality of filters positioned at equidistant positions around a perimeter of the vessel.

According to at least one embodiment, the system further comprises at least one condenser in communication with an interior of the vessel and is configured to condense sparge bubbles.

According to another embodiment, the system further comprises a mixing system positioned within the interior of the vessel.

In accordance with certain embodiments, the at least one blower is configured to deliver air at a pressure of 20 psi.

In accordance with one or more embodiments, a system for providing gas to a fermentation process is provided. The system comprises: a fermentation broth and at least one gas blower in fluid communication with the fermentation broth.

According to another embodiment, the at least one gas blower includes a gas production portion configured to generate gas and a gas delivery portion configured to provide the gas to the fermentation broth.

Still other aspects, embodiments, and advantages of these example aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Embodiments disclosed herein may be combined with other embodiments, and references to "an embodiment," "an example," "some embodiments," "some examples," "an alternate embodiment," "various embodiments," "one embodiment," "at least one embodiment," "this and other embodiments," "certain embodiments," or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

FIG. 13B-1 is a top view of a first impeller of the mixing system featured in FIG. 13A;

FIG. 13B-2 is a side view of the first impeller;

FIG. 13C-1 is a top view of a third impeller of the mixing system featured in FIG. 13A;

FIG. 13C-2 is a side view of the third impeller;

DETAILED DESCRIPTION

Figure 1:
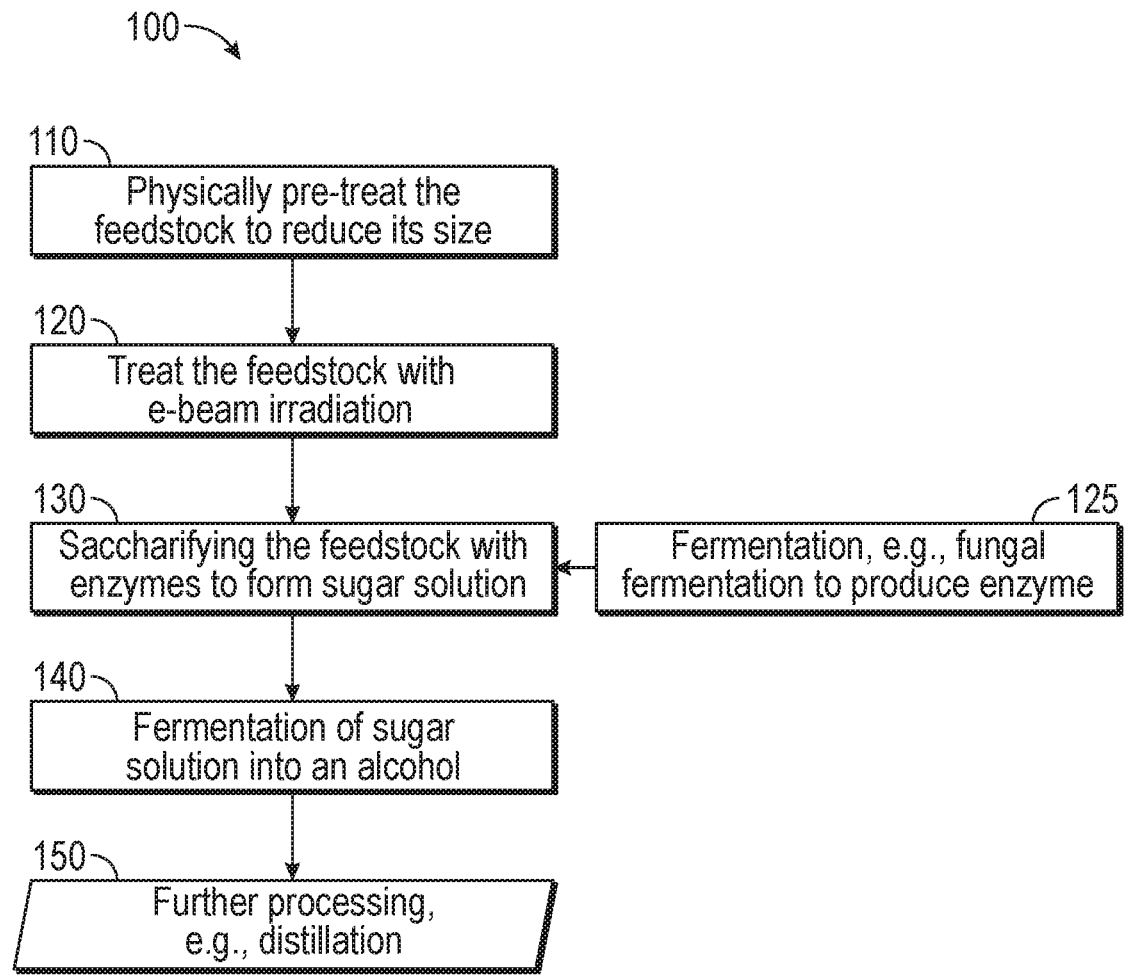
FIG. 1 is a process flow diagram illustrating conversion of a biomass feedstock to one or more products in accordance with one or more aspects of the disclosure.

In accordance with one or more embodiments, methods and systems for fermentation, e.g., aerobic fermentation, are provided. According to one embodiment, the system includes at least one blower or turbine that is used in combination with a gas, such as air, and may include a diffuser, such as a sparge tube, for example, a cylindrical or circular sparge tube, to introduce air bubbles into a vessel, e.g., a fermentation vessel containing a fermentation broth, e.g., including one or more microorganisms, such as one or more fungal cells. The methods and systems disclosed herein provide a more cost-effective and efficient process for introducing a gas, e.g., air, into a process, such as a fermentation process. The improved system, e.g., aerobic fermentation system, may therefore reduce the operating costs of a fermentation, especially when the fermentation time is very long, e.g., days or even weeks. For example, the power requirements for delivering 1000 CFM (cubic feet per minute) at STP (standard temperature and pressure) using the blower or turbine system as disclosed herein is typically in the range of about 25-50 kW. In contrast, the same air that is supplied using a rotary compressor system will require power in the range of about 150-200 kW. For a 15,000 gallon fermentation vessel operating at 0.5 vvm (vessel volumes per minute, which in this case is 7500 gallons per minute or roughly 1000 CFM, and using an average cost of about $0.10 per kWH, the costs are about $2.50/hour, or $60/day, or $600 for a 10-day fermentation. A typical manufacturing plant may do 1000 such fermentations a year, which would cost about $600,000 for the electricity costs associated with the air. In contrast, the yearly costs for a rotary compressor system would be about six times that amount, or about $3,600,000.

The aspects disclosed herein in accordance with the present invention, are not limited in their application to the details of construction and the arrangement of components set forth in the following description or illustrated in the accompanying drawings. These aspects are capable of assuming other embodiments and of being practiced or of being carried out in various ways. Examples of specific implementations are provided herein for illustrative purposes only and are not intended to be limiting. In particular, acts, components, elements, and features discussed in connection with any one or more embodiments are not intended to be excluded from a similar role in any other embodiments.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls. Moreover, titles or subtitles may be used in the specification for the convenience of a reader, which shall have no influence on the scope of the present invention.

In accordance with certain embodiments, the fermentation processes described herein may be part of a larger process, generally indicated at 100 in FIG. 1, which is a flow diagram illustrating conversion of biomass feedstock to one or more products. In one particular embodiment, at act 110, the feedstock may be physically pretreated to reduce its size, which is followed by e-beam irradiation to reduce its recalcitrance at act 120. At act 130, the feedstock is saccharified with one or more enzymes that may be produced via a fermentation process, as discussed below in reference to act 125, to form a sugar solution. The sugar solution is then bioprocessed at act 140 in a fermentation process to produce a desired product, such as alcohol or an organic acid, such as lactic acid, a salt of lactic acid, succinic acid or a salt of succinic acid. Thus, according to various aspects, the fermentation system disclosed herein may be used for any fermentation product, such as either the fermentation process at act 125 or at act 140. As noted in FIG. 1 at act 125, enzyme can be provided by a fermentation process (e.g., an aerobic fermentation), such as a fungal cell fermentation process, e.g., using *Trichoderma reesei* (*T. reesei*) such as strain RUT C30. Fungal cell fermentation processes can proceed for many days, e.g., 1, 2, 3, 4, 5, 6, 7, 8, 9, 10, or even 12 days or longer, and so reducing the cost of the provided air is advantageous to the cost of the enzyme. The resulting product from the fermentation process may be subjected to further processing, such as distillation, SMB (simulated moving bed) chromatography, or a form of electrodialysis, to produce a final product at act 150. According to some embodiments, saccharification and fermentation may be performed in the same vessel.

Fermentation Overview

Figure 2:
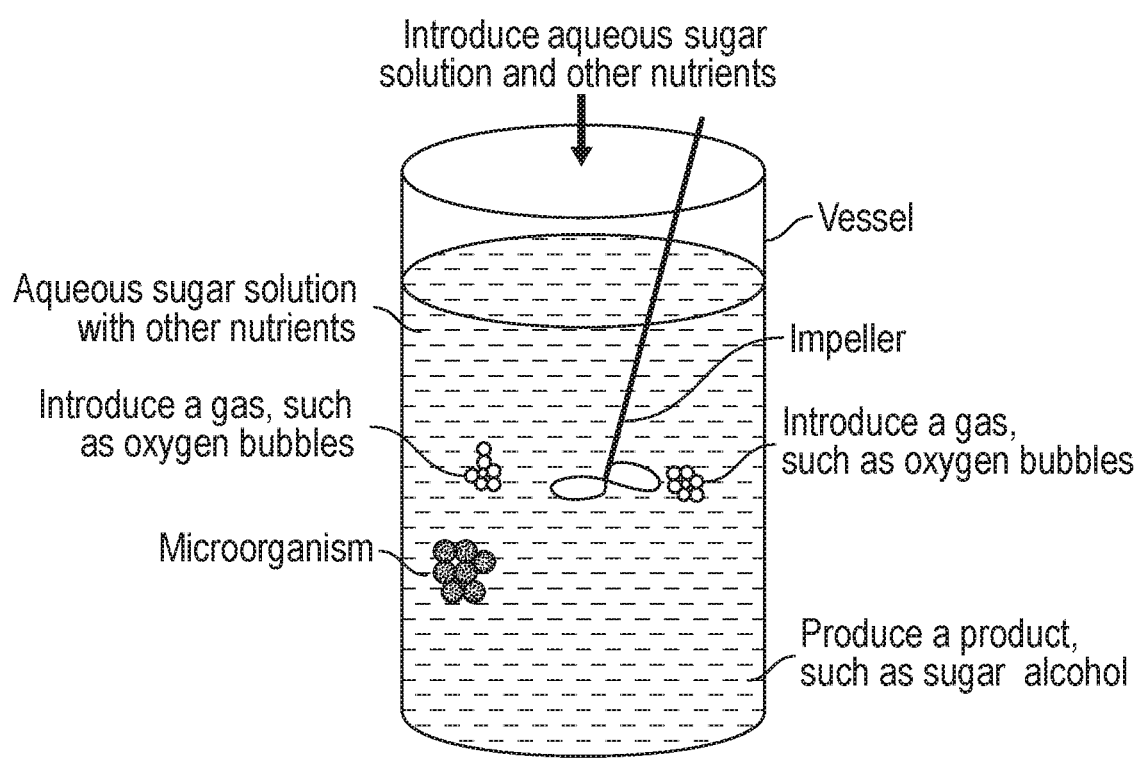
FIG. 2 is a schematic representation of the conversion of sugar into carbon dioxide gas and a sugar alcohol in accordance with one or more aspects of the disclosure.

In accordance with one or more embodiments, fermentation is a biological process in which molecules, such as sugars, such as glucose, fructose, and sucrose are converted into other molecules, such as alcohols and metabolic products, such as carbon dioxide and energy, in the form of heat. For example, glucose and/or xylose can be fermented using one or more bacteria, such as a lactobacillus to lactic acid, or glucose and a nitrogen source can be co-fermented to produce peptides or polypeptides, such as proteins or enzymes. As shown in FIG. 2, for example, aqueous sugar solution is introduced into a vessel, and during fermentation the aqueous sugar solution, which functions as a carbohydrate substrate, is inoculated with a microorganism under aerobic conditions. The optimum generation of the microorganism requires solution of oxygen in the aqueous sugar solution to be at a rate sufficient to replace oxygen consumed by the metabolic process. The rate of generation of the microorganism, and hence the production capacity of the anaerobic vessel is largely limited by the rate of oxygen in solution. As shown in FIG. 2, oxygen, in the case of an aerobic fermentation, may be introduced as fine bubbles into the aqueous sugar solution, which, as discussed further below, may be created by an air diffuser such as a sparge tube. In the case of an anaerobic fermentation, the gas introduced can be, for example, carbon dioxide, nitrogen, argon, or even methane. Mixing of the solution may be provided by an impeller, into the aqueous sugar solution. Often the impeller (or at least one of the impellers in a mixing system) utilized is suitable for "beating" the air or other gas into solution because gases generally have a low solubility in liquids, for example on the order of 8 mg/L for the case of air in water. Such an impeller is often called a radial flow impeller and examples include Rushton impellers. The rate of oxygen solution is primarily a function of bubble surface area and time of bubble-aqueous sugar solution contact. Generally, the oxygen transfer rate may be improved by reducing bubble size, increasing shear, for example, by using a radial flow impeller, increasing residence time, such as making a reactor with a high L to D ratio, or sandwichinHg a Rushton impeller between a down-pumping (on the top) and a up pumping (on the bottom) impeller. Other techniques are available, such as using air with an enhanced oxygen level or pure oxygen (in the case of an aerobic fermentation) or by reducing the temperature of the fermentation and thereby increasing the solubility of gases in the fermentation broth.

According to various embodiments, sugars, such as those produced by saccharifying a cellulosic or lignocellulosic feedstock, and other molecules, such as nitrogen sources, may be converted to one or more useful products, such as alcohols, such as sugar alcohols, e.g., erythritol or xylitol, or other alcohols, such as butanol. Other products, such as citric acid, lysine, glutamic acid, proteins, and enzymes can also be produced by contacting various fermentation broths with one or more microorganisms. For example, *Clostridium* spp. may be used to convert sugars, such as fructose or glucose, to butanol. *Clostridium* spp. may also be used to produce ethanol, butyric acid, acetic acid, and acetone. *Lactobacillus* spp. may be used to produce lactic acid. Other microorganisms, as discussed further below, may also be used during fermentation, including yeast and *Zymomonas* bacteria. In accordance with various aspects, saccharification may be partially or fully completed to produce a mixture that is subjected to fermentation.

According to various aspects, the fermentation process converts various nutrients, such as an aqueous sugar solution produced from the saccharification process to one or more products, such as a sugar alcohol. Non-limiting examples of such products include glycol, glycerol, erythritol, threitol, arabitol, xylitol, ribitol, mannitol, sorbitol, galactitol, iditol, inositol, volemitol, isomalt, maltitol, lactitol, maltotriitol, maltotetraitol, polyglycitol, butyric acid, gluconic acid, citric acid, and polyols, such as glycerin, pentaerythritol, ethylene glycol, and sucrose. Other products may include amino acids, peptides, polypeptides, proteins, and enzymes.

Fermentation System Components

Figure 3:
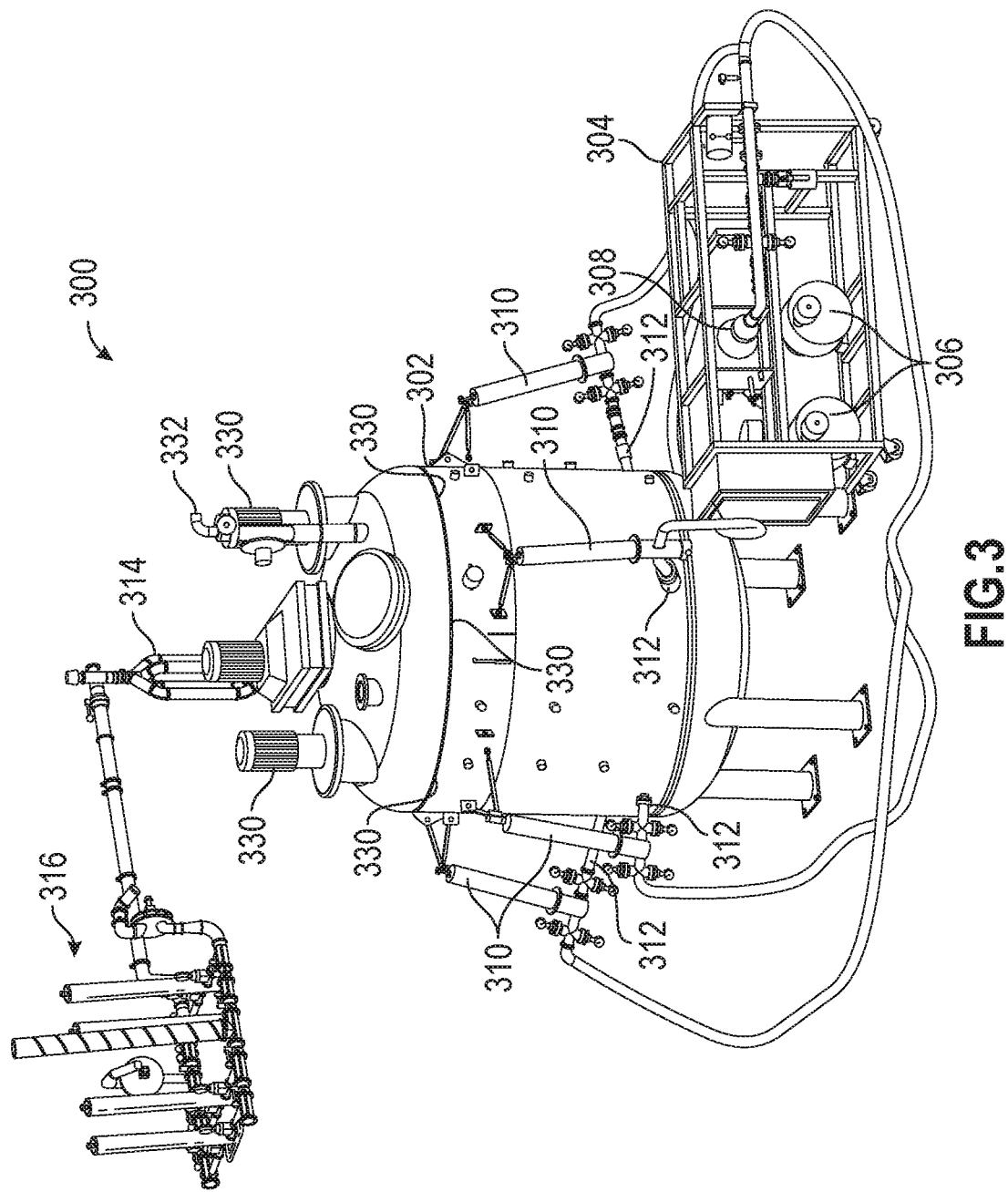
FIG. 3 is a perspective view of a fermentation system in accordance with one or more aspects of the disclosure.

Referring to FIG. 3, a fermentation system in accordance with one or more aspects of the disclosure and generally indicated at 300, is illustrated. As discussed further below, the fermentation system 300 may include a vessel 302, a blower skid 304 that includes one or more blowers 306, at least one inlet filter apparatus 310 for incoming air generated by the blower(s) 306, at least one sparge tube 312, a condenser 314, and an outlet filtration assembly 316.

Vessel

In accordance with various aspects, fermentation, such as fungal, bacterial or yeast cell fermentation, may be partially or completely performed in a vessel 302, as shown in FIG. 3. In certain embodiments, the aqueous sugar solution and/or other nutrients or fermentation additives may be introduced to an inlet of the vessel, also referred to herein as a feed stream inlet, that may be positioned at the top of the vessel, the bottom of the vessel, or anywhere in between that is suitable for accomplishing the fermentation methods described herein. As used herein, the term "vessel" broadly means any structure suitable for confining one or more process components, including gas, liquid and solid components and mixtures thereof. According to some embodiments, the vessel may be sized to have a volume of at least 1000 gallons. For example, the vessel may be sized to have a volume of 1500 gallons. According to another example, the vessel may be sized to have a volume of 2500 gallons. According to other embodiments, the vessel may be sized to have a volume of at least 10,000 gallons. For instance, the vessel may be sized to have a volume of 15,000 gallons. According to some embodiments, the vessel may be sized to have a volume of at least 100,000 gallons.

Figure 14:
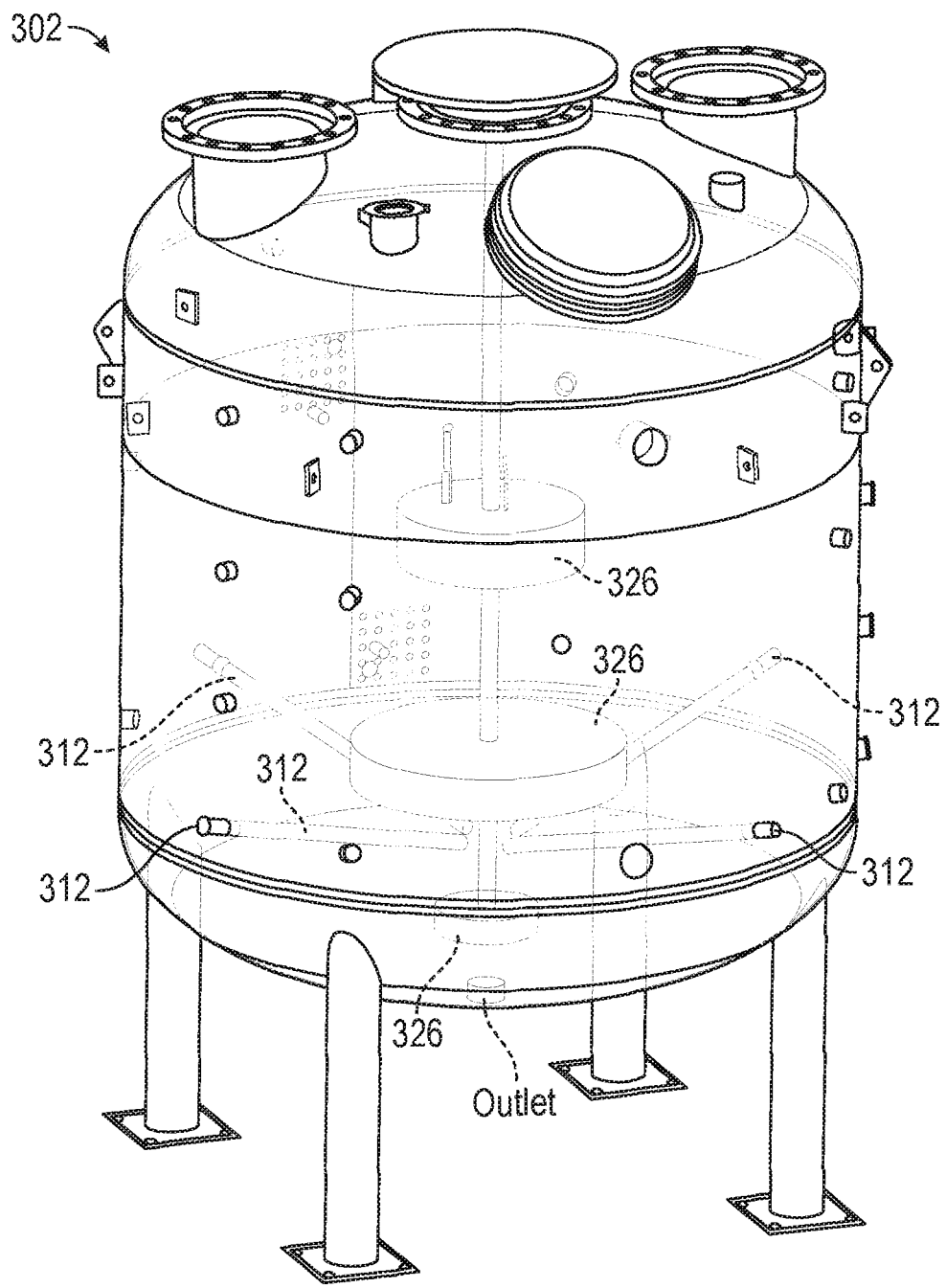
FIG. 14 is a perspective view of the interior of a fermentation apparatus in accordance with one or more aspects of the disclosure.

In accordance with certain embodiments, the vessel may not be highly pressurized, for example, not a certified ASME pressure vessel. According to certain embodiments, the pressure in the vessel may not exceed 12 psig, e.g., less than 10, 9, 8, 7, 6, 5, 4, 3.5, 3, 2.5, 2, 1.5, or less than 0.5 psig. According to other embodiments, the vessel may be closed or partially closed to operate under pressure, such as above 1 bar, 1.5, 2.0, or 2.5 bar. In certain applications, the vessel may be constructed to provide an anaerobic or aerobic environment for the components such as the fermentation broth. The vessel may be sized and shaped according to a desired application and volume of feed to provide a desired volume of product output. The vessel may also comprise at least one outlet (as shown in FIG. 14), where product, such as sugar alcohol, protein(s), or enzyme(s), may be removed from the vessel.

According to various embodiments, the vessel may be constructed of any material suitable for the purposes of the methods and systems described herein. Non-limiting examples of suitable materials include steel, stainless steel, hastelloy, titanium, and aluminum. One or more embodiments may include a vessel having one or more sidewalls depending upon the desired shape of the vessel. For example a cylindrical vessel may have one sidewall while a square or rectangular vessel may have four sidewalls. In certain embodiments, the vessel may have a cylindrical shape having one continuous sidewall positioned between the first and second walls. In certain other embodiments, the vessel may be closed wherein one or more sidewalls extend between a first wall and a second wall. In accordance with at least one embodiment, the vessel may be sized and shaped to have an aspect ratio L/D of 2:1 or less, e.g., 1.8/1, 1.6/1, 1.4/1, 1.2/1, 1/1, 0.8/1, 0.6/1, or less than 0.5/1. According to other embodiments, the vessel may have an aspect ratio of 1:1. According to certain aspects, the size and shape of the vessel may be designed to optimize or otherwise enhance the fermentation process. For example, a vessel with an aspect ratio of 2:1 may reflect the ratio of the volume of aqueous sugar solution to the volume of incoming air. For instance, a 12,000 gallon tank has a process requirement of 6000 gallons of air that needs to be pumped in. Likewise, a 50,000 gallon tank needs 25,000 gallons of air. According to certain embodiments, a maximum height of the vessel, measured as an average distance from the sparge tubes to the top of the fluid level is not more than 40 feet, e.g., less than 38, 37, 35, 33, 31, 29, 27, 25 or less than 20 feet when the blower is capable of generating 25 psig or less, e.g., less than 20, less than 19, 18, 17, 16, or 15 psig.

Sparge Tubes

One or more sparge tubes 312 or diffusers may also be positioned at various positions about the vessel 302. Although the sparge tubes 312 are shown to be external to the vessel 302 shown in FIG. 3, each sparge tube 312 connects to the inlet filter apparatus 310 and extends into the vessel and functions to inject fine bubbles into the fermentation broth for the purposes of stimulating growth of the microorganisms. According to various embodiments, the sparge tube may be constructed from a specially sintered porous metal material. The sintered sparge tube materials may be made by performing a hot isostatic pressing process, where high isostatic pressure is applied to constituent powdered materials in a perform at elevated temperatures, and the annealing process is terminated before completion. This results in a porous material that is suitable for creating fine bubbles. Non-limiting examples of suitable porous metals used for the sparge tube include stainless steel, stainless steel alloys (such as AISI 316L), titanium, nickel, and nickel alloys. According to some embodiments, the sparge tube is constructed from a porous metal element, a threaded fitting, and in certain instances, a reinforcement rod. The sparge tubes may be flange-mounted to the side of the vessel. Sparge elements can be many different shapes, including cylindrical or circular in shape. In specific embodiments, the sparge element is circular in shape, and is distributed about the entire tank. According to certain embodiments, the pore size of the sparge tube is less than 100 microns, e.g., less than 90, 80, 70, 60, 50, 40, 30, 20, 15, 14, 13, 12, 11, 10, 9, 8, 7, 6, 5, 4, 3, 2, 1 or even less than 0.9 micron, e.g., 0.8, 0.7, 0.6, 0.5, 0.4 or even less than 0.25 microns. According to certain embodiments, for example to minimize pressure drop, the porosity of the sparge element is greater than 50 percent, e.g., greater than 60, 70, 80, 85, 88, 90 or even greater than 95 percent porosity. As shown in FIG. 3, four sparge tubes 312 may be positioned at equidistant locations around the perimeter of the vessel 302. The sparge tubes 312 may also be positioned to introduce air into a lower portion of the vessel 302 and the bottom of the fermentation broth held within, which allows for a more efficient distribution of air, as opposed to placing the air inlets near the top of the vessel 302. As will be appreciated, the number of sparge tubes may be increased or decreased according to the size of the vessel and the process requirements. The sparge tubes may be configured to create micro-sized bubbles in one direction, multiple directions, or in all directions, such as in a 360 degree arrangement.

Figure 15A:
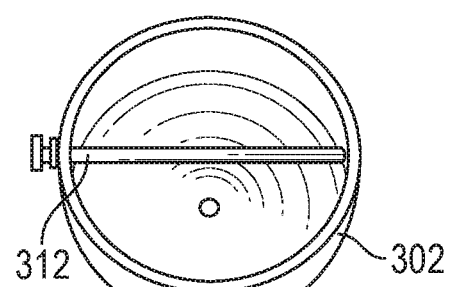
FIG. 15A is a top view of one example of a sparge tube configuration in accordance with one or more aspects of the disclosure.
Figure 15B:
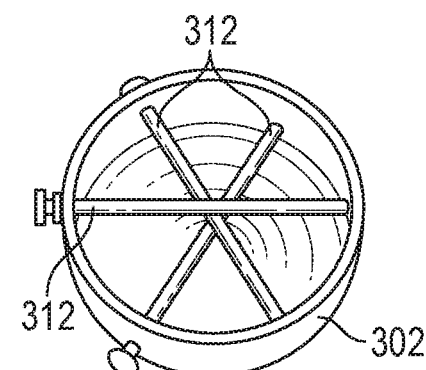
FIG. 15B is a top view of a second example of a sparge tube configuration in accordance with one or more aspects of the disclosure.
Figure 15C:
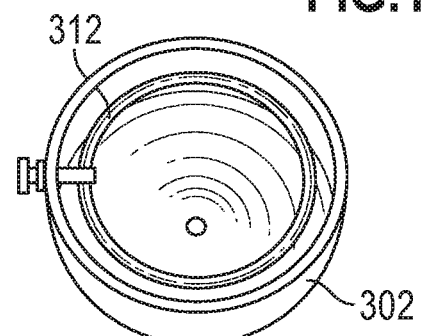
FIG. 15C is a top view of a third example of a sparge tube configuration in accordance with one or more aspects of the disclosure.
Figure 15D:
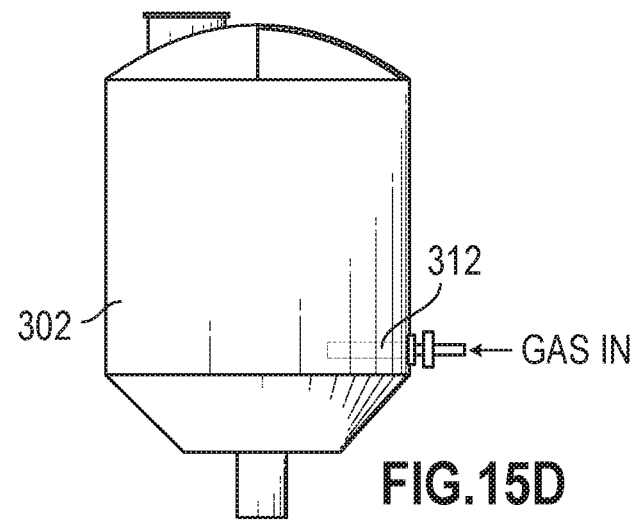
FIG. 15D is side view of a sparge tube attached to a vessel in accordance with one or more aspects of the disclosure.

Referring to FIGS. 15A-15D, several different examples of sparge tubes are shown that are suitable for one or more of the processes and systems disclosed herein. FIG. 15D is a general illustration of how the sparge tube 312 is attached to a vessel 302. The configuration shown in FIG. 15A is a top view of an example of one sparge tube positioned within a tank 302, and the configuration shown in FIG. 15B is a top view of an example of several sparge tubes positioned within a tank 302. The sparge tubes of FIGS. 15A and 15B are generally cylindrical in shape, and extend into the vessel 302 in linear or straight lengths, and in this instance the sparge tubes expand across the entire width of the vessel, although, other lengths are also within the scope of this disclosure, such as the sparge tubes shown in FIG. 14, which extend partially (and slightly downward) into the vessel. In contrast, the sparge tube shown in FIG. 15C is bent to extend in a circular shape that generally follows the circumference of the interior of the vessel. As shown, the sparge tube of this configuration may be positioned in close proximity to the interior walls of the vessel 302.

Blower Skid Components

In accordance with one or more embodiments, the fermentation system may include a blower skid 304, as shown in FIGS. 3-6, that supplies a gas, such as oxygen or air, to the fermentation broth in the vessel 302. The blower skid 304 includes at least one blower 306 and a heat exchanger 308. The blower skid 304 may also include at least one pressure gauge, 318 and 324, at least one temperature gauge 320, and at least one flow meter 322.

According to some embodiments, the fermentation system 300 may include at least one power operated blower 306. Each centrifugal gas turbine-driven blower 306 includes a driver motor equipped with a rotor that spins at high speeds and functions to discharge gas, such as air, into the vessel. In accordance with at least one embodiment, each blower may be sized according to the process requirements and the size of the vessel. For example, according to one embodiment, each blower may include a 12.5 hp motor. The size of the blower dictates the amount of air in cubic feet per minute that can be sparged into the vessel. As noted above, a 12,000 gallon vessel may have a process requirement of 1000, 2000, 3000, 4000, 5000, or 6000 or more gallons of air per minute, which in turn dictates the sizing of the blowers. For example, in accordance with various aspects, fermentation may be performed with aeration using a sparging tube, as discussed above, and an air and/or oxygen supply to maintain the dissolved oxygen level above about 10%, such as above 20%. Further, the air requirement may be distributed to multiple blowers instead of using one single blower, since the single blower may be significantly more expensive to purchase and operate. For example, the fermentation system of FIG. 3 uses two 11 kW blowers instead of a single 22 kW blower. Further, the blower may be selected to operate with a maximum psi. For instance, the blower may produce a maximum pressure of 20 psi. According to some embodiments, a suitable blower may be available from Spencer Turbine Co., Windsor, CT, such as a SPENCER® POWER MIZER® Series 2500 blower, including the Spencer Model Number CS21R96. The use of one or more blowers to drive air into the vessel is more cost effective and more efficient than using compressors. For example, compressors are expensive to manufacture, maintain, and operate, and may incur energy costs that are at least four times, e.g., six times, that of one or more blowers.

In accordance with at least one embodiment, the air exiting the blower(s) 306 passes through a water-cooled heat exchanger 308 before entering the inlet filter apparatus 310 (discussed further below) and the vessel 302. According to some embodiments, multiple heat exchangers may be utilized. For example, one heat exchanger may be used for course tuning and a second heat exchanger may be used for fine tuning the exiting temperature of the gas. For instance, the first heat exchanger may run a cooling fluid, such as water, that is at a temperature between 80° F. and 110° F., such as between 85° F. and 100° F., and the second heat exchanger may run a fluid that is at a temperature of less than 65° F., e.g., less than 60° F., 58° F., or less than 55° F. According to some embodiments, air entering the blower 306 may be at room temperature (~25° C.), and is then heated to a temperature of 200° F. or more by the blowers. According to various embodiments, the heat exchanger 308 functions to cool down the air or other gas entering into the vessel 302 so that it does not kill the organisms and/or raise the temperature of the batch or other processing occurring in the vessel. Thus, air entering the heat exchanger 308 may be at a temperature of 200° F. or more, which is then cooled down to a temperature below 100° F., such as 90° F., 85° F., 80° F., and in certain instances, back to room temperature of 25° C. by the heat exchanger 308. The size of the heat exchanger 308 is a function of the flow rate of air going into the vessel 302. Other cooling fluids besides water used by the heat exchanger 308 may include refrigerant and cryogenic liquids. The heat exchanger 308 may be a shell and tube heat exchanger, where coolant fluid flows inside the tubes, and the air or other gas flows across the fins. As will be recognized by one of ordinary skill in the art, other types of heat exchangers are also within the scope of this disclosure. According to some embodiments, the heat exchanger 308 is a tube and fin type heat exchanger. For example, both the tubes and the fins may be constructed from stainless steel, or the tube may be constructed from stainless steel and the fins may be constructed from aluminum material. In still other embodiments, the tubes and the fins may be made from copper.

Figure 4:
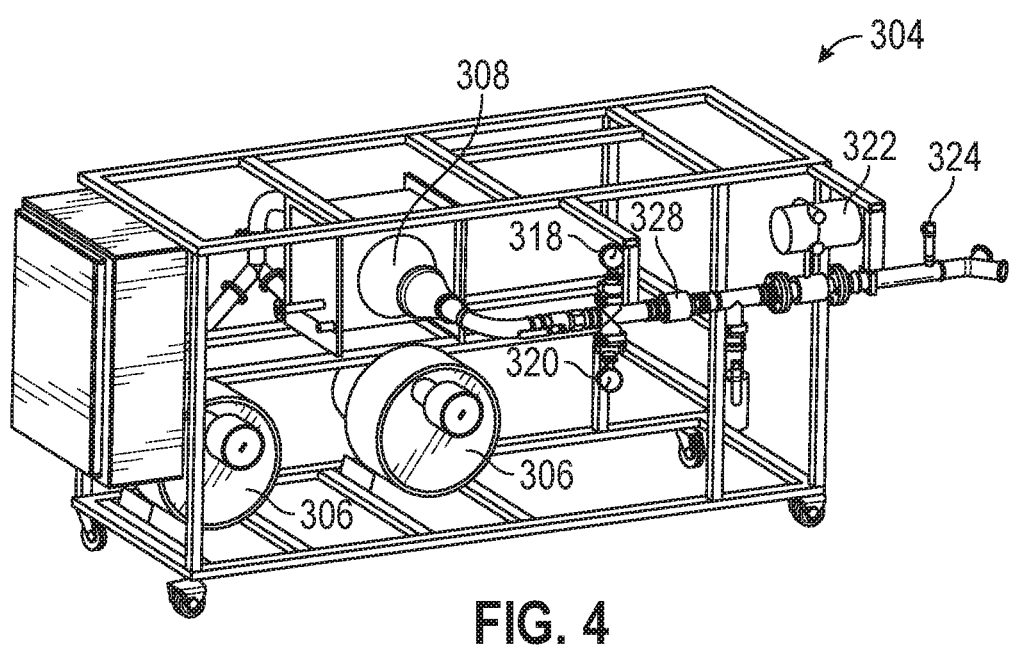
FIG. 4 is a perspective view of a blower skid in accordance with one or more aspects of the disclosure.
Figure 5:
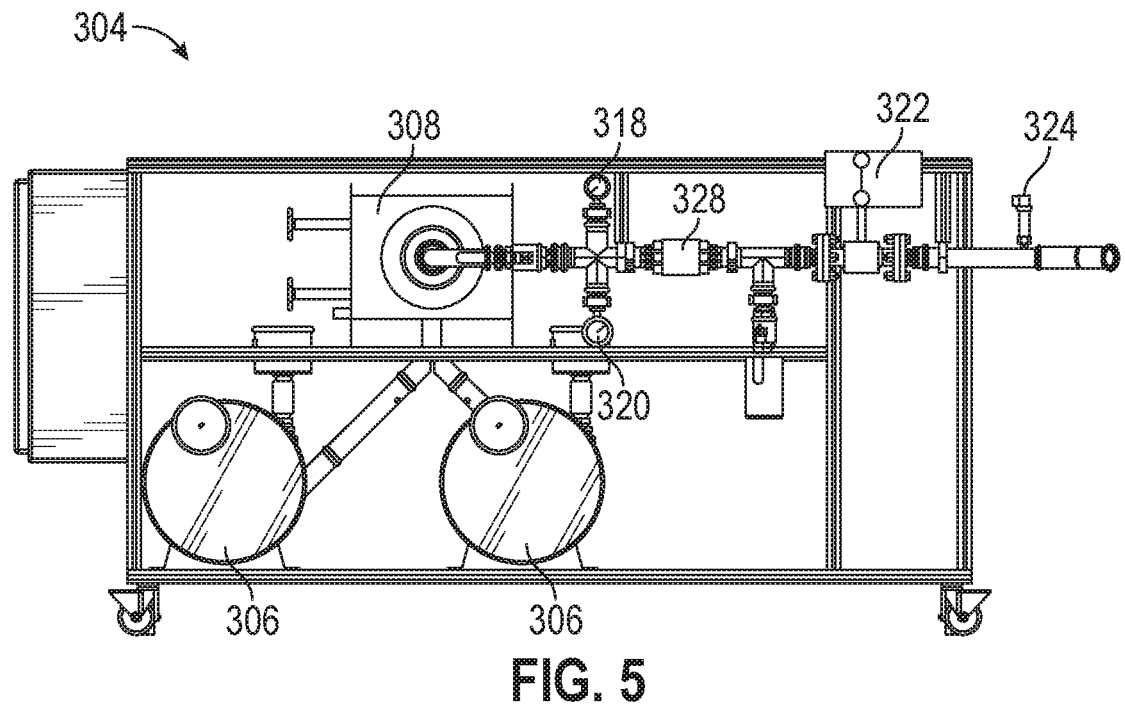
FIG. 5 is a side view of the blower skid featured in FIG. 4.
Figure 6:
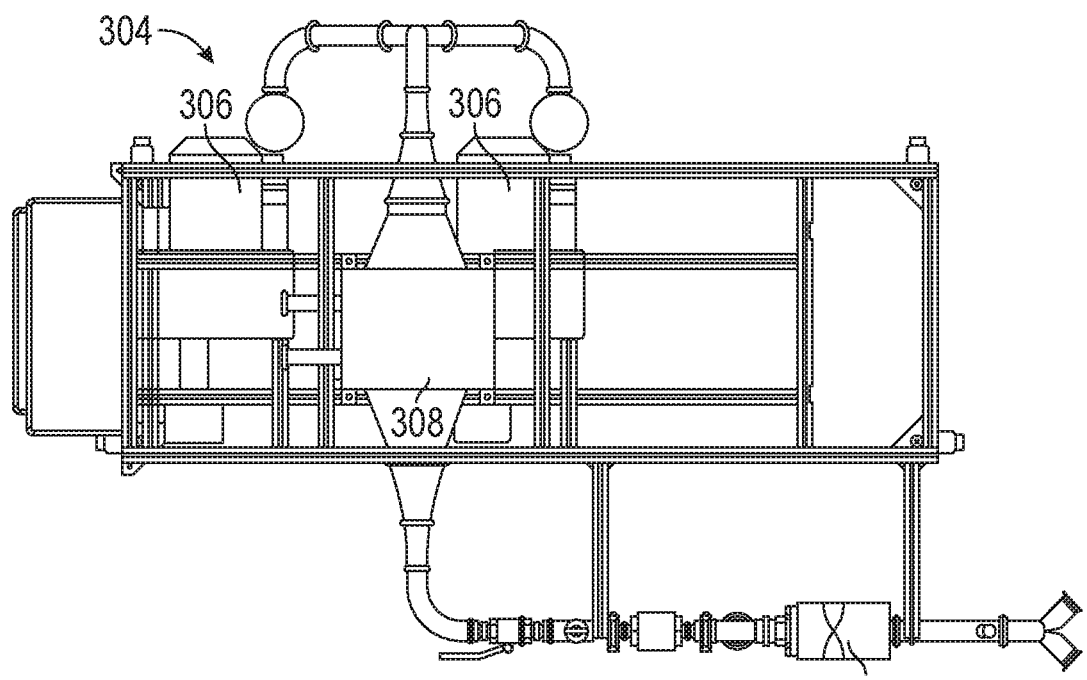
FIG. 6 is a top view of the blower skid featured in FIG. 4.

As shown in FIGS. 3-5, the blower skid 304 may also include one or more pressure gauges 318 and 324, temperature gauges 320, and flow meters 322. For instance, temperature and pressure readings may be taken of the heated air exiting the blower by temperature gauge 320 and pressure gauge 318. As shown in FIGS. 4 and 5, a check valve 328 may be also be included in the blower skid assembly to prevent reverse flow. The flow rate of the air moving to the fermentation vessel 302 may be measured by the flow meter 322. A second pressure gauge 324 may also measure the pressure of the air before it is split into multiple flowpaths and distributed to the inlet filter apparatuses 310, as discussed further below.

Inlet Filter Apparatus

Figure 8:
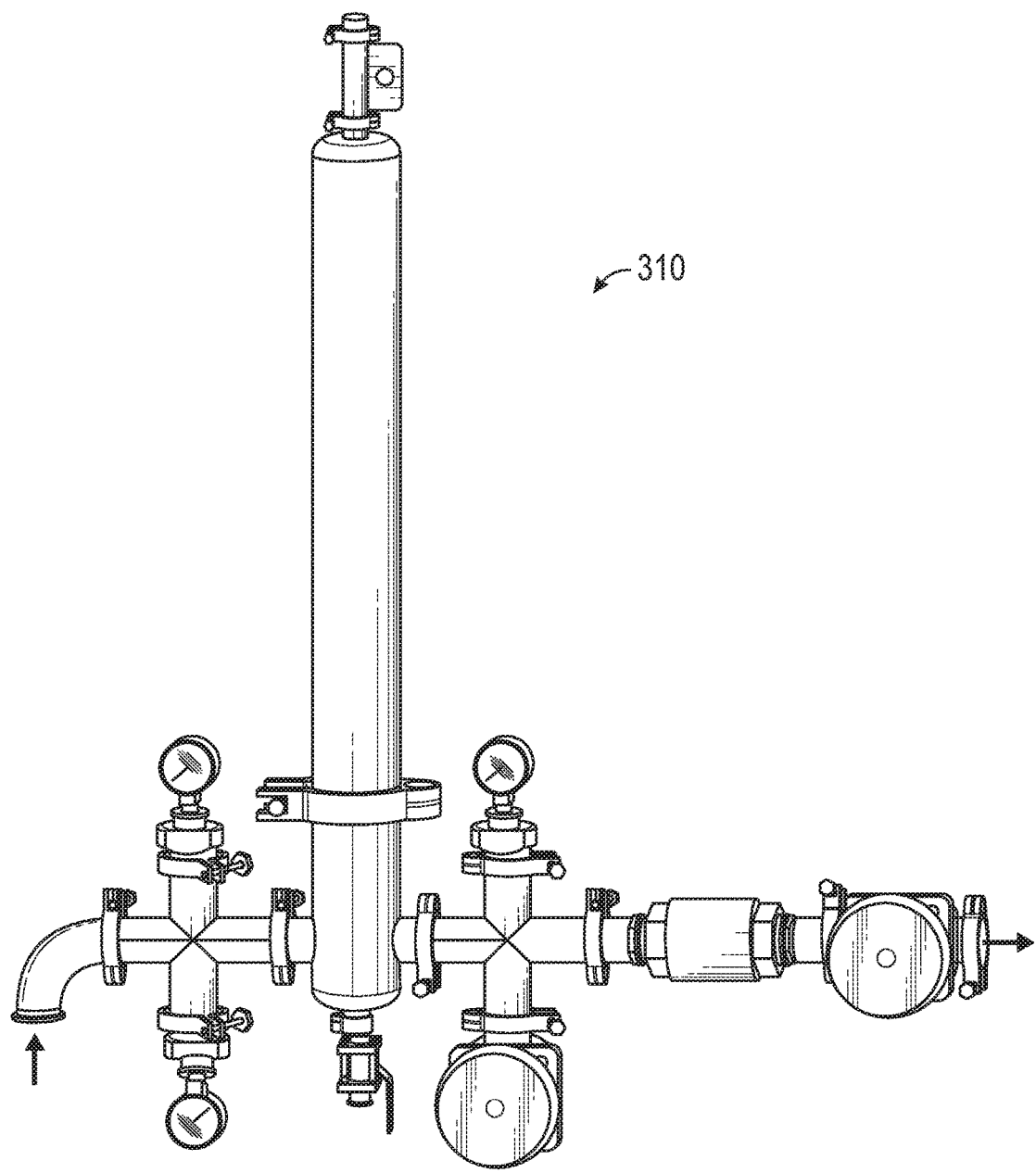
FIG. 8 is a perspective view of an inlet filtration apparatus in accordance with one or more aspects of the disclosure.
Figure 9:
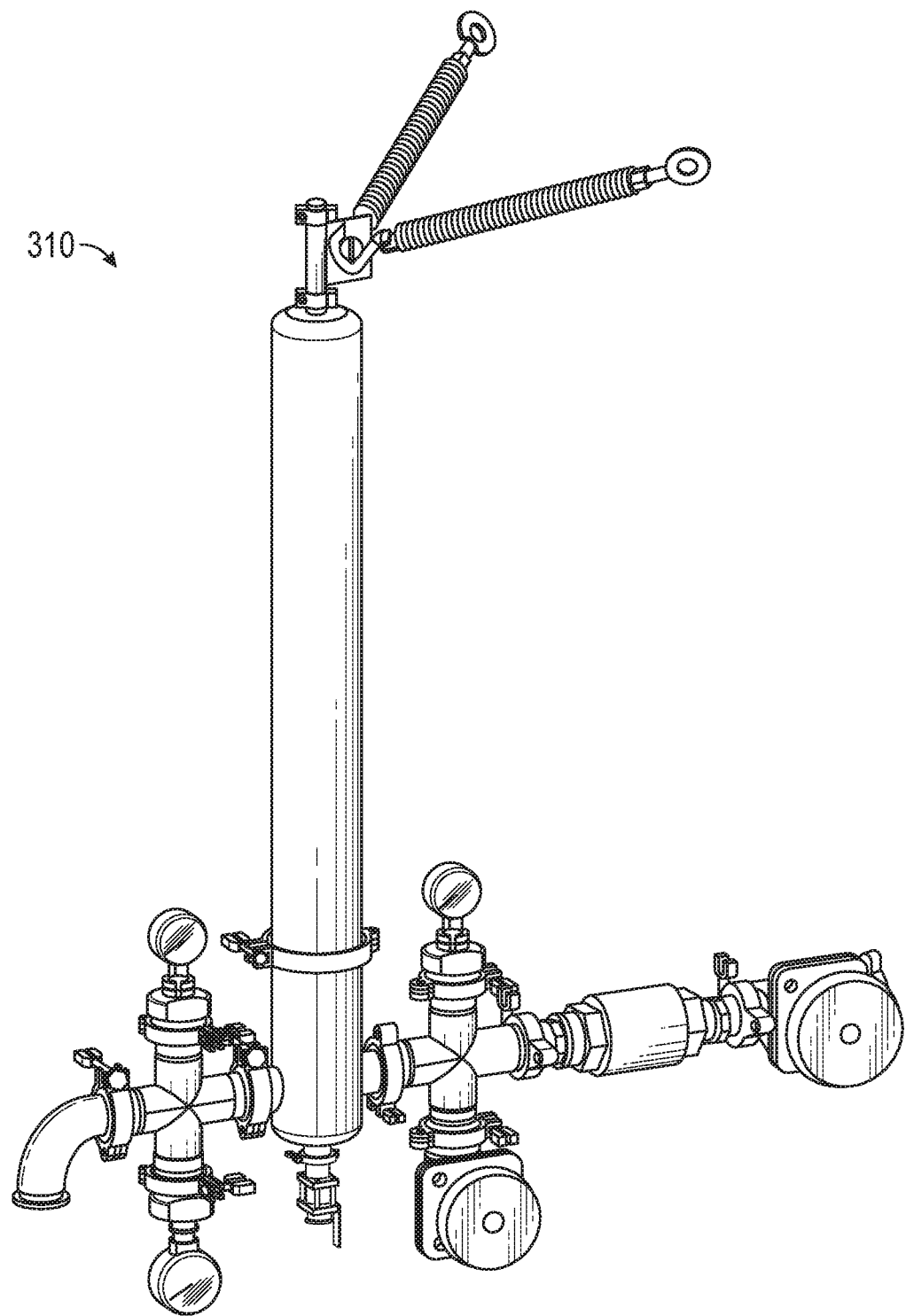
FIG. 9 is another perspective view of the inlet filtration apparatus featured in FIG. 8.

According to certain embodiments the fermentation system includes at least one filter apparatus 310, also referred to herein as an inlet filter apparatus, as shown in FIGS. 3, 8, and 9. Gas such as air or oxygen that exits the blower 306 and heat exchanger 308 and is introduced into the fermentation process may first need to be sterilized so as to not interfere with the fermentation chemistry. According to the embodiment shown in FIG. 3, air exiting the blower skid assembly 304 is split into multiple flowpaths, such as the four separate flowpaths shown in FIG. 3, using flexible conduits. Each of the flexible conduits may be sized to avoid creating large pressure drops. For example, the flexible conduits may be sized to have a diameter that is at least two inches. Each flowpath is equipped with a filter apparatus 310, as shown more clearly in FIGS. 8 and 9. Each filter apparatus may include a membrane filter. The porosity of the membrane filter may be from about 50 percent to about 95 percent, e.g., between about 60 percent and about 80 percent and the pore size may be between about 0.1 microns and 2 microns, such as between 0.2 microns and 1 micron. For example, warmed air from the blower skid assembly 304 may be forced through a filter that removes air particles and bacteria and many viruses down to 0.2 microns. Placement of the inlet filter apparatus 310 at the outlet side of the blower skid 304, including the heat exchanger 308, rather than at the inlet side before the blower, assures that air passing through the filter is under positive pressure relative to ambient. Any leak following or before the filter will therefore not serve as a path for particulate entry to the airstream. The membrane may be constructed from any one or more hydrophobic materials, including polymers. Suitable filters include the EMFLON® polytetrafluoroethylene (PTFE) filter (Pall Corporation, East Hills, Long Island, New York).

The inlet filter apparatus 310 may include several other components besides the membrane filter. For example, FIGS. 8 and 9 illustrate a pressure and temperature gauge that may be used to measure the pressure and temperature of the incoming air from the blower skid 304. This air may pass through the filter, where it is sterilized. A second pressure gauge measures the pressure of the air exiting the filter, before it is sent through a check valve (to prevent backflow and contamination) and onward into the vessel 302.

Referring to FIG. 3, the fermentation system 300 may include four inlet filter apparatuses 310 that are positioned at equidistant positions around the perimeter of the vessel 302, as described above in reference to the sparge tubes 312. The number of inlet filter apparatuses 310 may be a function of one or more process parameters, such as the volume of fermentation broth that is to be treated, the type of microorganism used in the process, which may dictate the necessary amount of air or oxygen needed for the process, and the size and/or shape of the tank. As shown in FIG. 3, each inlet filter apparatus 310 may be configured to connect to a sparge tube 312 that extends into the vessel 302. In some embodiments, the sparge tube 312 may connect to the inlet filter apparatus 310 at a position external to the tank, such as in instances where the sparge tube includes a fluid-tight connector that may be used for mating different components of the system together. In other embodiments, the sparge tube 312 is positioned completely within the interior of the vessel 302, so that a connecting region, such as a pipe, extends through the vessel 302 and connects to the filter apparatus at one end and connects to the sparge tube 312 at the other end. The top of the inlet filter apparatus 310 may also include one or more cables or other attachment means that can be used to attach and stabilize the top of the filter cartridge to the vessel 302, as shown in FIGS. 3, 8, and 9.

Condenser for Vessel

Figure 10A:
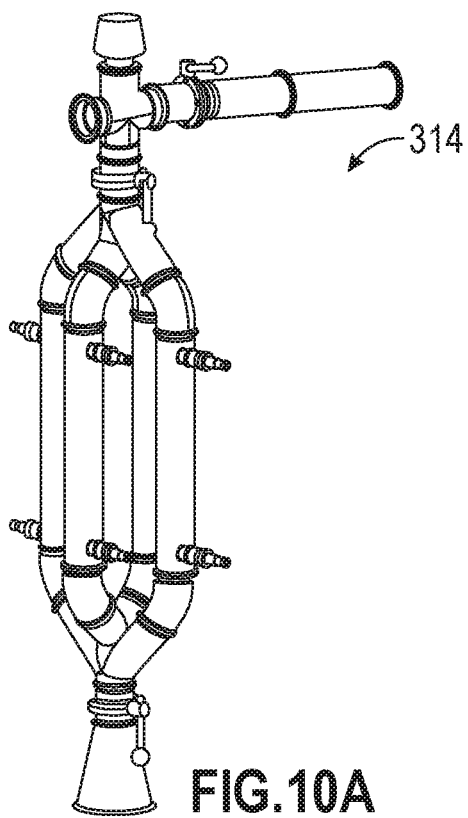
FIG. 10A is a perspective view of a condenser in accordance with one or more aspects of the disclosure.
Figure 10B:
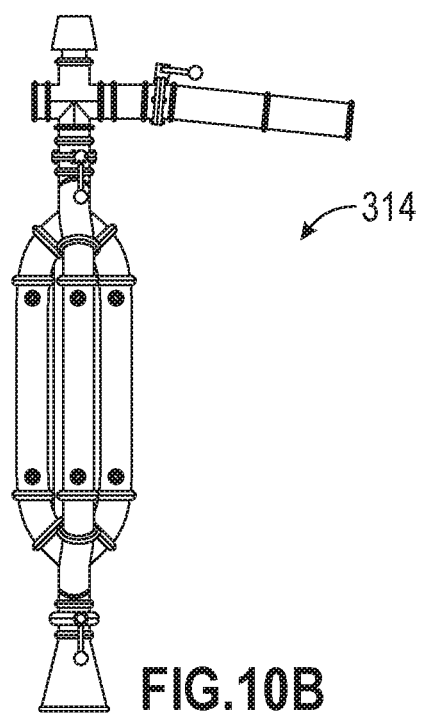
FIG. 10B is a side view of the condenser featured in FIG. 10A.
Figure 11:
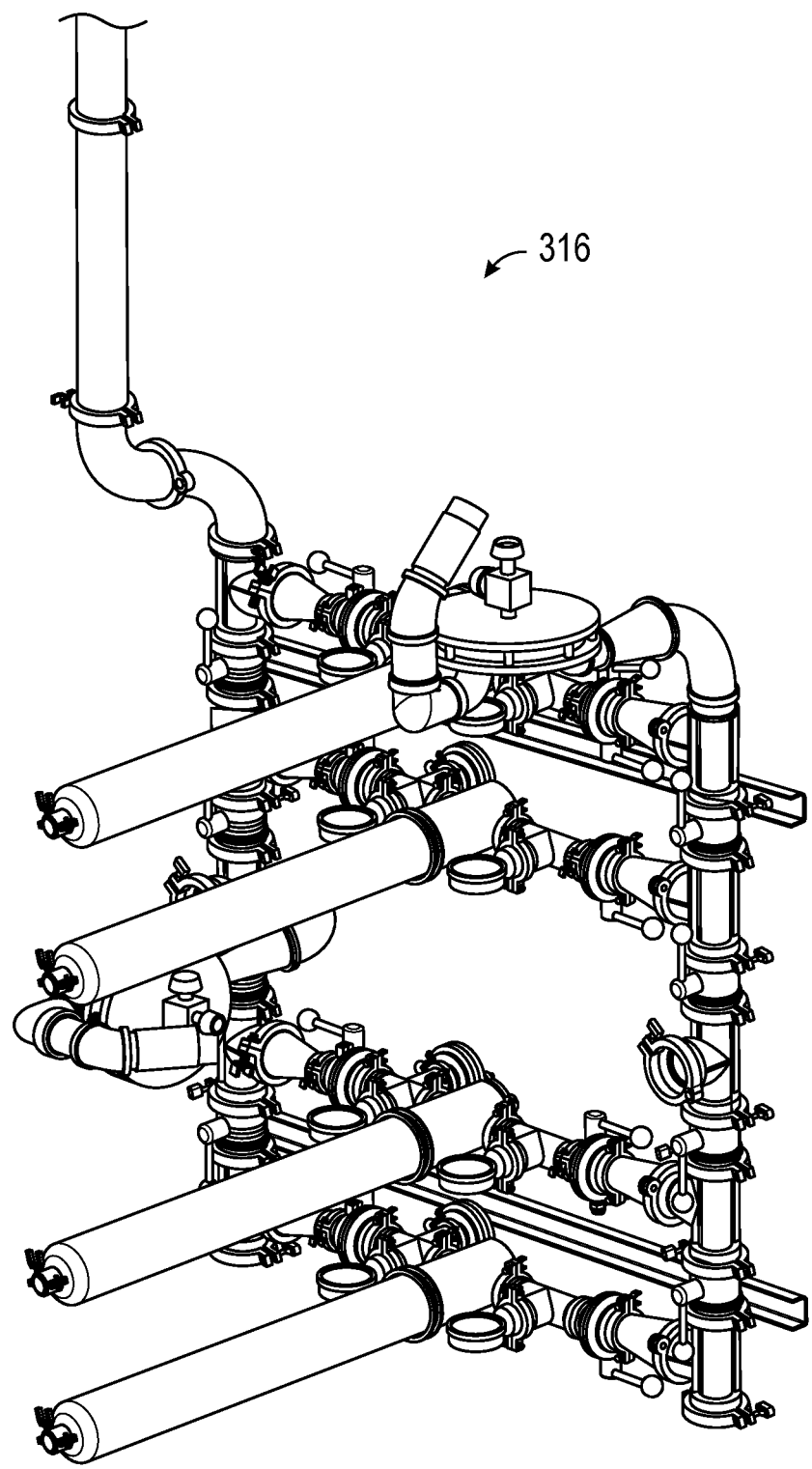
FIG. 11 is a perspective view of an outlet filtration assembly in accordance with one or more aspects of the disclosure.
Figure 12:
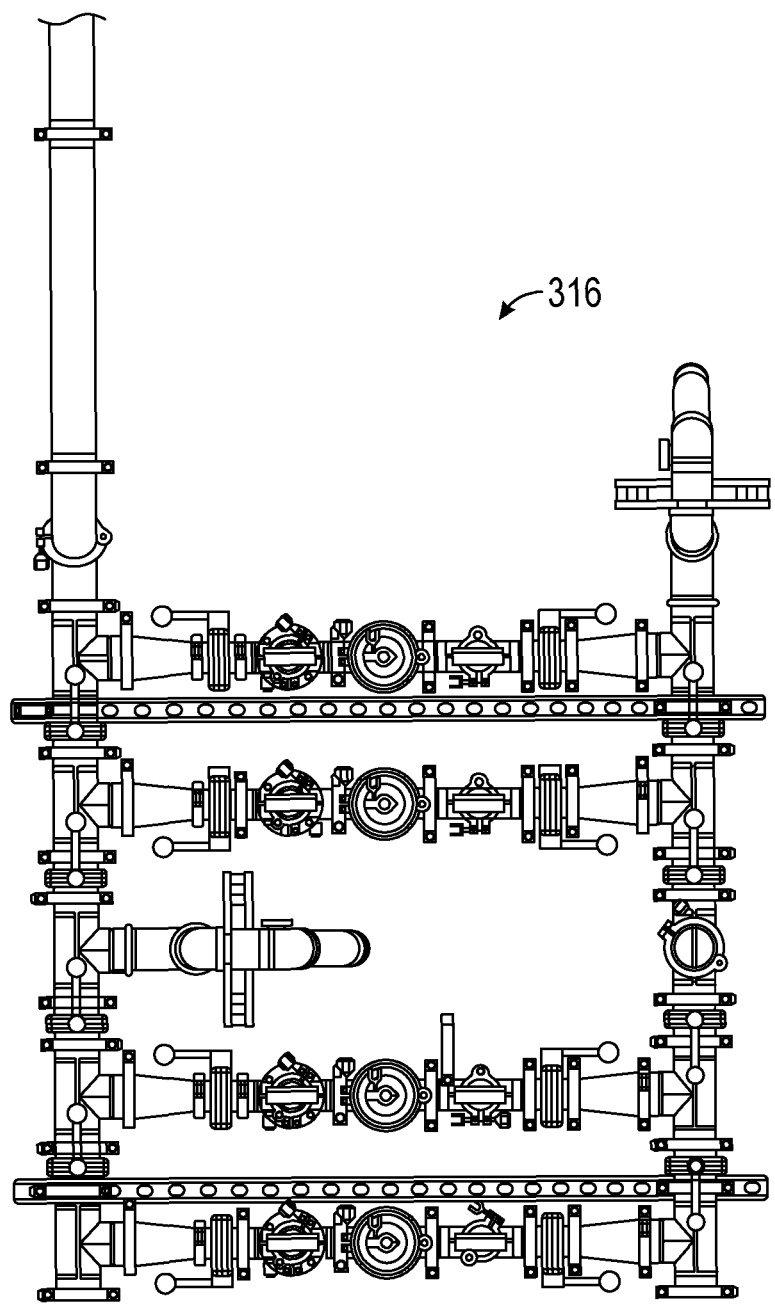
FIG. 12 a top view of the outlet filtration assembly featured in FIG. 11.

According to various embodiments, the fermentation system 300 may also include a condenser 314, which functions to condense fluid back into the tank. The condenser 314 is illustrated in FIGS. 3, 10A, and 10B. Pressure within the vessel 302 created from sparging causes water to discharge from the vessel 302. In addition, water particles atomized during sparging need to be contained or otherwise prevented from entering the outlet filtration assembly 316 (discussed below), so as to prevent water from condensing in the filters. Therefore, the condenser 314 may be positioned at the top of the vessel and used to condense the sparge bubbles that float from the bottom to the top of the vessel 302. According to various aspects, the condenser 314 may be equipped with multiple tubes that are cooled by the surrounding ambient air; thereby allowing the sparge bubbles to condense as water, and flow back into the vessel 302. According to certain embodiments, air exiting the condenser 314 is further heated so as to drive off any moisture before it enters the outlet filtration assembly 316.

In accordance with some embodiments, the condenser may be a shell and tube condenser. According to some embodiments, the condenser is a tube and fin type condenser. For example, both the tubes and the fins may be constructed from stainless steel, or the tube may be constructed from stainless steel and the fins may be constructed from aluminum material (for greater efficiency). In still other embodiments, the tubes and the fins may be made from copper.

Outlet Filtration Assembly

In accordance with at least one embodiment, the fermentation system 300 includes a filtration assembly 316, also referred to herein as an outlet filtration assembly. The outlet filtration assembly may serve a number of functions, including keeping bacteria and other contaminants from reverse-flowing back into the vessel 302. The outlet filtration assembly 316 may include several filters, such as those discussed above in reference to the inlet filter apparatus 310. According to certain embodiments, the outlet filtration assembly 316 may be in fluid communication with the condenser 314 via a conduit, which may be heated. For example, not all water escaping from the vessel may be captured and re-condensed back into the vessel by the condenser 314. Therefore, additional water may be heated in the conduit so as to evaporate all remaining liquid. In accordance with some embodiments, air that exits the outlet filtration assembly vents to the atmosphere, and in certain instance may be vented to an external environment.

Impeller/Agitator for Vessel

Figure 13A:
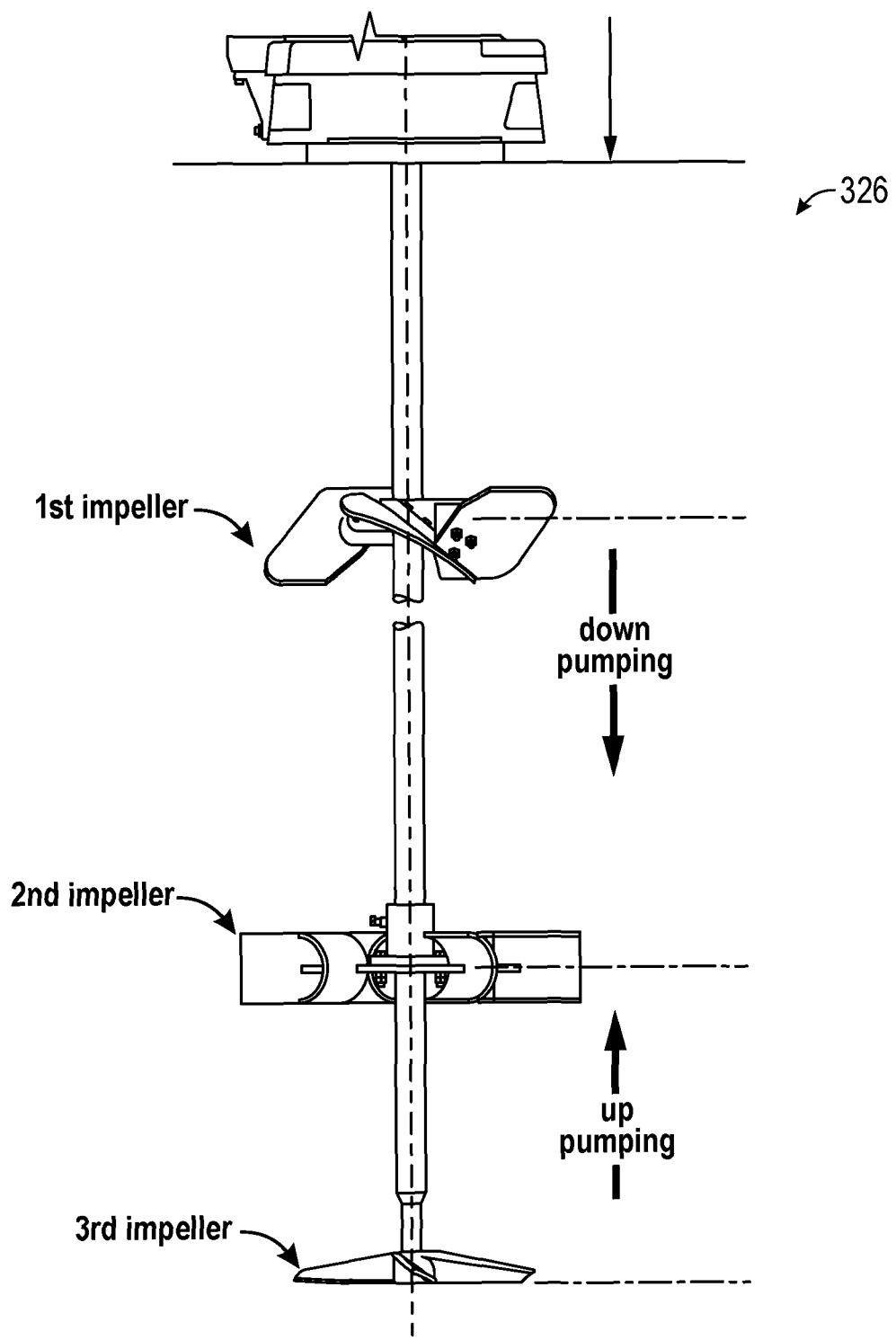
FIG. 13A is a side view of a mixing system in accordance with one or more aspects of the disclosure.
Figures 1, 13B:
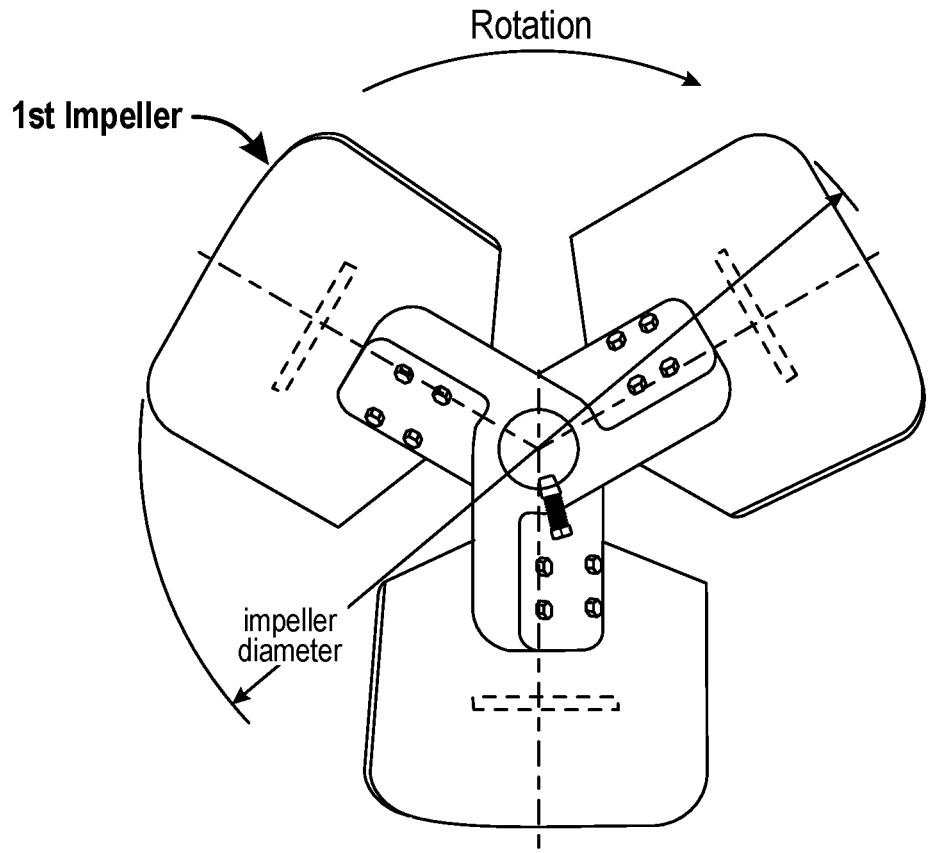
Figures 2, 13B:
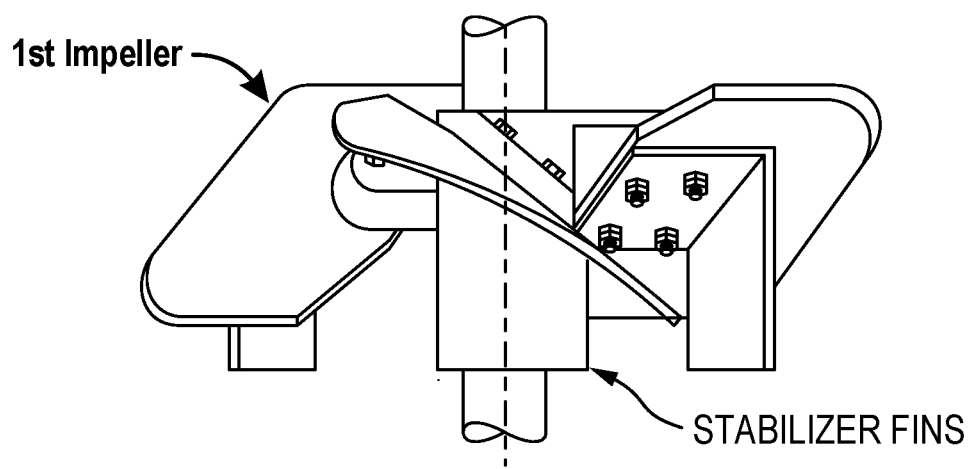
Figures 1, 13C:
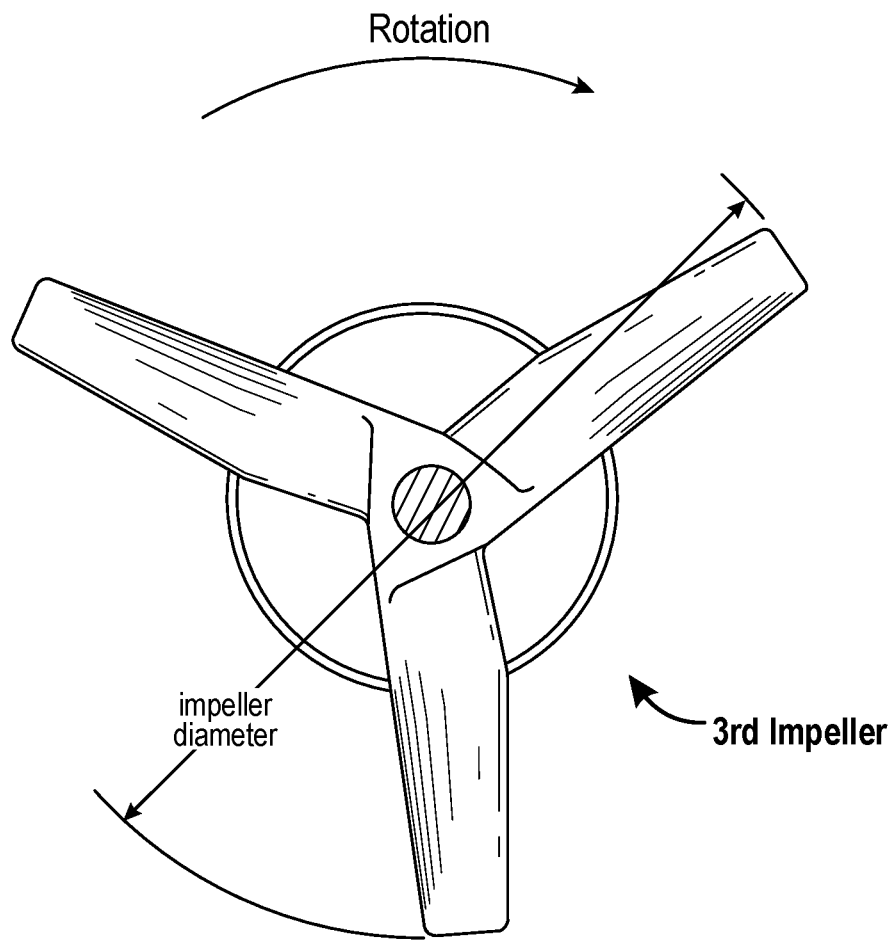
Figures 2, 13C:
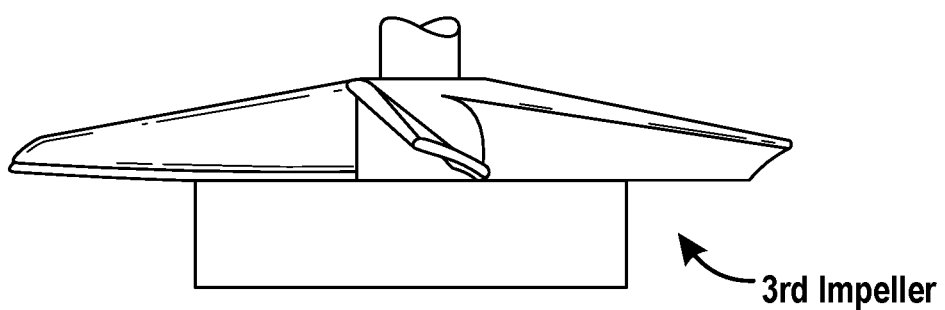

In reference to FIGS. 13A, 13B-1, 13B-2, 13C-1, and 13C-2, the interior of the vessel may be equipped with a mixing system 326 that functions to mechanically mix the contents of the vessel and to maximize oxygen transfer. According to some embodiments, the mixing system 326 may include one or more impellers. The mixing system 326 may be vertically positioned in the center of the vessel 302. The mixing system 326 may be driven by a motorized central shaft that includes vertically-positioned impeller blades. For example, as shown in FIG. 13A, a first impeller may be positioned in an upper portion of the interior of the vessel, a second impeller positioned near the center of the vessel, and a third impeller may be positioned in a lower portion of the vessel. A top and side view of the first impeller are shown in FIGS. 13B-1 and 13B-2, respectively, and a top and size view of the third impeller are shown in FIGS. 13C-1 and 13C-2, respectively. Each impeller may be configured to serve a different function. In the configuration shown in FIG. 13A, the first (top) and third (bottom) impellers increase residence time of air sparged into the vessel by keeping air trapped in the spacing between these two impellers. For instance, the bottom impeller is configured to create a lifting or rising force, which is counteracted by the pushing or lowering force of the top impeller. The second, middle impeller may be a Rushton turbine, as discussed above, which creates radial-flow high shear forces that "beat" or otherwise enhance gas dissolution into the surrounding fermentation broth. The speeds used for each of the impellers may depend on the size of the vessel and the type of processing. For example, the speed of the impellers for a 2500 gallon tank may be less than 100 rpm, for example, less than 80, 70, 60, or less than 50 rpm. The impeller blades are constructed from a material that does not interfere with the chemical fermentation process, such as a metal, including steel or a metal alloy. The mixing system 326 may also be equipped with a variable speed controller, so that speed of one or more of the impellers can be adjusted during the fermentation process. A motor, such as a 15 hp motor, may be used to drive the central shaft.

The mixing system 326 may be sized and shaped to fit within the interior of the vessel 302. For instance, according to one example, the first impeller may have a diameter of 23 inches (584 mm), the second impeller may have a diameter of 34 inches (864 mm), and the third impeller may have a diameter of 12.8 inches (325 mm). Further, the distance between the horizontal center line of the first impeller and the horizontal center line of the second impeller may be 30 inches (762 mm) and the distance between the horizontal center line of the second impeller and the horizontal center line of the third impeller may be 22 inches (559 mm). The diameter of the shaft above the first impeller and extending down through the second impeller may be 2.5 inches (64 mm). The section of the shaft above the third impeller may have a diameter of 1.5 inches (38 mm). As will be appreciated, other sizes and configurations of the mixing system 326 and its components are also within the scope of this disclosure. The sizes may be varied according to the size of the vessel and the type of application.

In reference to FIG. 14, an interior of a fermentation vessel 302 is shown that includes a mixing system 326 that includes three vertically-positioned impeller blades, such as those discussed above in reference to FIG. 13A, which appear as cylinders in FIG. 14. Also included is a view of four sparge tubes 312 positioned around the perimeter of the vessel 302 and extend slightly downward into a central bottom portion of the vessel. As discussed above, each sparge tube 312 may deliver uniform small bubbles to the fermentation broth that promote the growth of the microorganisms in the fermentation broth.

Fermentation Process Overview and Conditions

Figure 7:
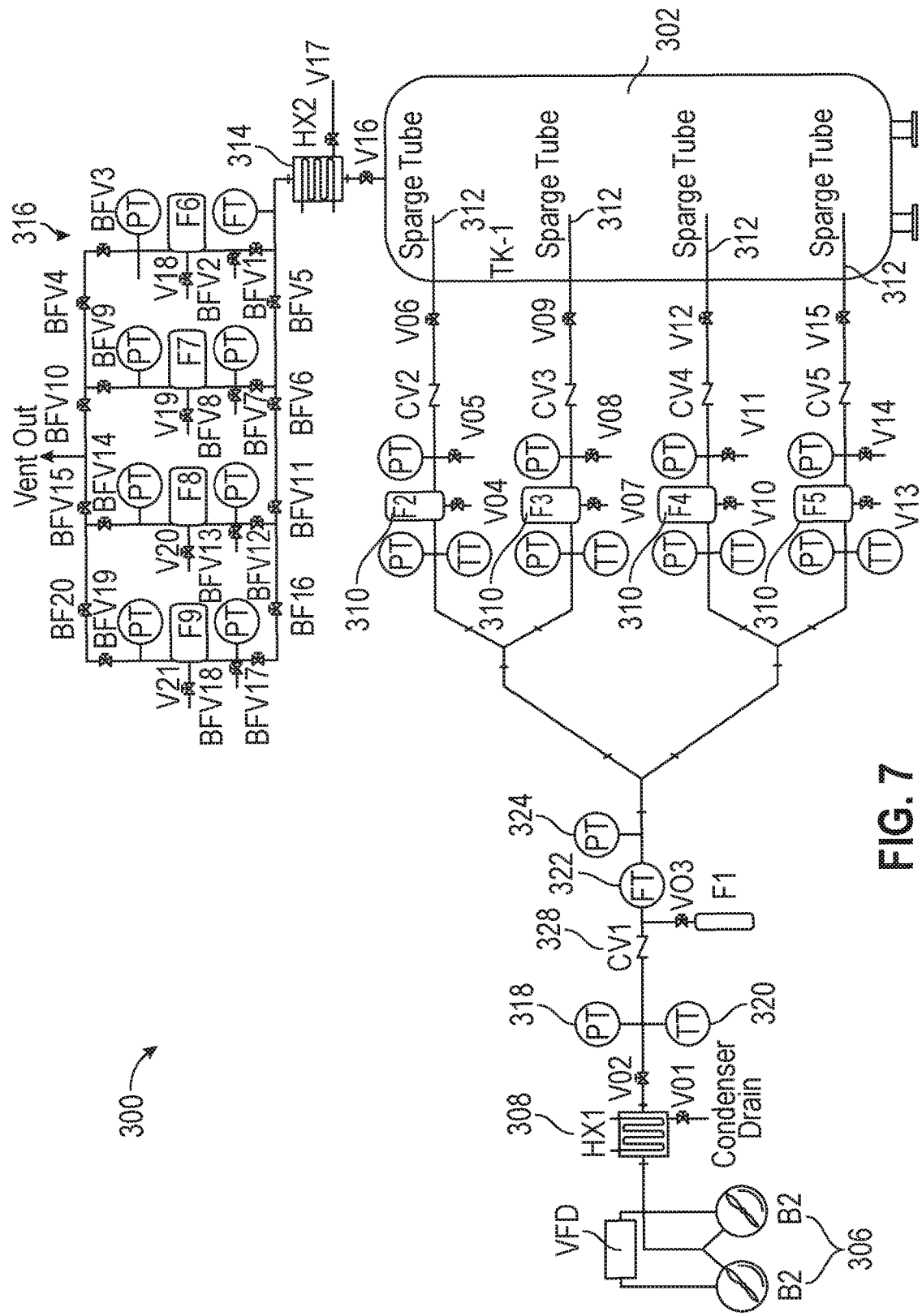
FIG. 7 is a schematic of the fermentation system featured in FIG. 3.

Referring to FIG. 7, a schematic representation of the aerobic fermentation system 300 shown in FIG. 3 is shown. During operation, aqueous sugar solution is pumped into the fermentation vessel 302 through an inlet (not shown in FIG. 7). In some embodiments, the inlet may be injected into one or more ports positioned in an upper portion of the vessel, and in certain instances, the broth may be introduced into any port that is above the fluid line within the vessel. According to some embodiments, the fermentation is performed using a glucose solution having an initial glucose concentration of at least 5 wt. % at the start of fermentation. Furthermore, the glucose solution can be diluted after fermentation has begun.

In accordance with various embodiments, the fermentation process may be performed according to a method of continuous operation using multiple batches. For example, the completion of a fermentation process may be indicated by one or more of the following properties of the fermentation broth: the concentration of nutrients, the concentration of one or more products, the pH, the amount of dissolved gas, and the fermentation time period.

According to certain aspects, a high initial sugar concentration at the start of fermentation may favor the production of sugar alcohols. Thus, the saccharified feedstock solution may be concentrated prior to combination with a microorganism that produces sugar alcohols to increase the glucose level of the solution. Concentration may be done by any desired technique, for example, by heating, cooling, centrifugation, reverse osmosis, chromatography, precipitation, crystallization, evaporation, adsorption, and combinations thereof. According to some embodiments, concentration is performed by evaporation of at least a portion of the liquids from the saccharified feedstock. In certain aspects, concentration increases the glucose content to greater than about 5 wt %, greater than about 10 wt. %, greater than about 20 wt. %, greater than about 30 wt. %, greater than about 40 wt. % and greater than about 50 wt. %.

According to at least one embodiment, the saccharified feedstock may be purified before or after concentration. Purification may be performed to increase the glucose content to greater than about 50 wt. % of all components other than water, such as greater than about 60 wt. %, greater than about 70 wt. %, greater than about 80 wt. %, greater than about 90 wt. %, and greater than about 99 wt. %. Purification may be performed by any technique known in the art, non-limiting examples including heating, cooling, centrifugation, reverse osmosis, chromatography, precipitation, crystallization, evaporation, adsorption, or any combination thereof.

Once in the vessel 302, the aqueous sugar solution may be contacted with one or more microorganisms, as discussed further below. According to at least one embodiment, the microorganisms are cannulated into the vessel from a prior process, such as from the final vessel of a seed train process. In some embodiments, the contacting step includes a dual stage process, comprising a cell growth step and a fermentation step. For example, a dual stage fermentation process may include an initial cell growth phase followed by a product production phase. In the growth phase, the process conditions may be selected to optimize cell growth, where as in the production phase, process conditions may be selected to optimized production of one or more desired fermentation products. Generally speaking, low sugar levels, such as those between 0.1 and 10 wt. %, or between 0.2 and 5 wt. % in the growth medium favors cell growth, and higher sugar levels, such as those greater than about 5 wt. %, greater than about 10 wt. %, greater than about 20 wt. %, greater than about 30 wt. %, and greater than about 40 wt. % in the fermentation medium favors product production. In addition, other process parameters may be modified for each stage. For example, temperature, agitation, sugar levels, nutrients, and/or pH may all be adjusted according to the stage of the process. In addition, process conditions may be monitored in each stage for the purposes of optimizing the process. For example, the cell growth stage of the process may be monitored to achieve an optimum density, for example, about 50 g/L, greater than about 60 g/L, greater than about 70 g/L, or greater than about 75 g/L, and a concentrated saccharified solution may be added to trigger the onset of product formation. Optionally, the process may be optimized, for example, by monitoring and adjusting the pH or oxygenation level with probes and automatic feeding to control cell growth and product formation. According to a further aspect, other nutrients may be controlled and monitored to optimize the process, such as amino acids, vitamins, metal ions, yeast extract, vegetable extracts, peptones, carbon sources and proteins.

Dual-stage fermentations are described in *Biotechnological production of erythritol and its applications*, Hee-Jung Moon et al., *Appl. Microbiol. Biotechnol.* (2010) 86: 1017-1025. In certain instances a high initial concentration of glucose at the start of the fermentation favors erythritol production, but if a high concentration is maintained for too long, it may be detrimental to the microorganism. A high initial glucose concentration may be achieved by concentrating glucose during or after saccharification as discussed above. After an initial fermentation period that allows the start of fermentation, the fermentation media may be diluted with a suitable diluent to bring the level of glucose below about 60 wt. %, below about 50 wt. %, or below about 40 wt. %. The diluent may be water or water with additional components such as amino acids, vitamins, metal ions, yeast extract, vegetable extracts, peptones, carbon sources and proteins.

Referring back to FIG. 7, the fermentation process may be performed with aeration using a sparging tube and an air and/or oxygen supply to maintain the dissolved oxygen level in the fermentation broth above about 10%, such as above 20%. This may be achieved by taking room temperature air and passing it through one or more blowers, which create the necessary force to push the air through the heat exchanger 308, the inlet filter apparatus 310, and the sparge tubes 312 positioned in the vessel 302. Air exiting the blowers is heated from room temperature to about 200° C. using heat exchanger 308, as described above, and then split into four flowpaths. Air passing through each flowpath is first passed through a 0.2 micron filter in the inlet filter apparatus 310 to remove contaminants, before being introduced into the fermentation broth through the sparge tube 312.

As discussed above, the fermentation vessel 302 may be sized and shaped to optimize one or more process conditions. For example, in certain instances the maximum air pressure that can be generated by the blower(s) 306 is 20 psi. In order to get this air to the top regions of the vessel 302, the vessel may be shorter, since a taller tank would create high hydrostatic pressure. According to some embodiments, the vessel may not be pressurized, but may be equipped with one or more steam jets that may be used for the purposes of sterilization. The steam may be injected using a large diaphragm valve, which may pressurize the vessel to about 0.5 psi, or in the alternative, the steam may be injected with one or more valves open to atmosphere, so that the vessel remains at atmospheric pressure.

Referring to FIG. 3, pressure in the fermentation vessel 302 may be controlled by one or more pressure relief valves 330 that include a pressure gauge. The pressure relief valve may be controlled by a controller, as discussed further below, and functions to release pressure from the vessel 302 when the pressure within the vessel 302 exceeds a predetermined value, such as 2 psi. The pressure relief valve 330 shown in FIG. 3 extends across the entire diameter of the tank and includes two pressure gauges positioned on the top of the vessel.

In accordance with various embodiments, jet mixing may be used during fermentation. The jet mixing may be performed by one or more impellers, such as the mixing system 326 discussed above in reference to FIG. 13A. The impeller(s) functions to mix the contents of the vessel 302 and to enhance oxygen transfer to the microorganisms.

In accordance with some embodiments, fermentation may be performed at a pH in a range of pH 4 to 7. The pH may be maintained in a certain range of values depending on the type of microorganism used. For example, when using yeast as a microorganism, the pH is maintained in a range of pH 4-5, whereas the pH is maintained in a range of pH 5-6 when Zymomonas is used. According to some embodiments, the pH of the fermentation broth is measured using a pH probe that is positioned in the side of the vessel. In certain embodiments, ammonium hydroxide may be added to maintain the pH at a desired level.

According to some embodiments, fermentation may be performed for a predetermined time. For example, the fermentation may be conducted from 24 to 168 hours, such as from 24 to 96 hours, or from 24 to 120 hours.

In accordance with various embodiments, fermentation is performed at temperatures in the range of 20° C. to 40° C. (e.g., 26° C. to 40° C.). The temperature may depend on the type of microorganism used. For example, thermophilic microorganisms prefer higher temperatures.

According to various embodiments, nutrients for the microorganisms may be added during the fermentation process. For example, food-based nutrient packages such as those described in U.S. Patent Application Publication No. 2012/0052536, the entire disclosure of which is incorporated herein by reference.

In accordance with various embodiments, the product from the fermentation process is isolated. For example, product may be extracted from one or more outlets of the vessel, which in certain instances may be positioned at the bottom of the vessel, as shown in FIG. 14.

As discussed above, a condenser 314 may be positioned at the top of the vessel 302 the functions to condense the sparge bubbles that float to the top of the vessel 302. Further, the vessel may also be equipped with at least one vent 332 that allows gases, such as carbon dioxide, oxygen, and/or air to escape the vessel 302.

According to some embodiments, the fermentation system includes a controller that may be used to control one or more aspects of the fermentation process and/or equipment. For example, each inlet filter apparatus 310 may be configured to measure the temperature and pressure of the incoming air or other gas into the vessel 302. Further, the rpm of each blower may also be monitored, as well as the pH and the amount of dissolved oxygen in the fermentation broth. A predetermined value or range of values may be desired for each of these process variables, and when the measured value falls below or above the predetermined value, the controller may be configured to adjust one or more aspects of the fermentation process. For example, if the level of dissolved oxygen in the fermentation falls below 10%, then the rpm of the blower may be increased to push more air into the vessel.

In accordance with certain embodiments, all or a portion of the fermentation process may be interrupted before the low molecular weight sugar is converted to an alcohol such as ethanol. Intermediate fermentation products include sugar and carbohydrates, which may be in high concentration. The sugars and carbohydrates may be isolated via any means known in the art. According to various aspects, these intermediate fermentation products may be used in the preparation of food for human or animal consumption. Additionally or alternatively, the intermediate fermentation products can be ground to a fine particle size, for example, using a stainless-steel laboratory mill, to produce a flour-like substance.

In accordance with one or more embodiments, a mobile fermenter may be used for the fermentation process, as described in International App. No. PCT/US2007/074028 and published as PCT Publication WO 2008/011598, the disclosure of which is hereby incorporated by reference in its entirety. According to a further embodiment, all or a portion of the fermentation process may be performed during transit.

According to other embodiments, anaerobic organisms may be used in the fermentation process. Thus, the fermentation process may be conducted in the absence of oxygen. The fermentation process may be conducted in the presence of one or more inert gases, such as nitrogen ($N_2$), argon (Ar), helium (He), carbon dioxide ($CO_2$), and mixtures thereof. Further, the fermentation mixture may have a constant purge of an inert gas flowing through the vessel during part or all of the fermentation process. According to one embodiment, carbon dioxide is used to achieve or maintain anaerobic conditions during the fermentation process, without any addition of any other inert gas.

Fermentation Agents

In accordance with various embodiments, the microorganisms used in the fermentation process may be naturally occurring microorganisms and/or engineered microorganisms. For example, the microorganism may be a bacterium, such as cellulolytic bacterium, a fungus, such as yeast, a plant, a protist, such as a protozoa or a fungus-like protist, such as a slime mold, or an alga. When the microorganisms are compatible, mixtures of microorganisms may be used for fermentation.

The microorganism used for fermentation may be any suitable microorganism capable of converting carbohydrates, such as glucose, fructose, xylose, arabinose, mannose, galactose, oligosaccharides, or polysaccharides into fermentation products. According to various aspects, the fermentation microorganisms include strains of the genus *Saccharomyces* spp. (including, but not limited to, *S. cerevisiae* (baker's yeast), *S. distaticus, S. uvarum*), the genus

*Kluyveromyces*, (including, but not limited to, *K. marxianus, K. fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii* (Philippidis, G. P., 1996, Cellulose bioconversion technology, in Handbook on Bioethanol: Production and Utilization, Wyman, C. E., ed., Taylor & Francis, Washington, D.C., 179-212)). Other suitable microorganisms include, for example, *Zymomonas mobilis, Clostridium* spp. (including, but not limited to, *C. thermocellum* (Philippidis, 1996, supra), *C. saccharobutylacetonicum, C. tyrobutyricum C. saccharobutylicum, C. Puniceum, C. beijernckii,* and *C. acetobutylicum*), *Moniliella* spp. (including but not limited to *M. pollens, M. tomentosa, M. madida, M. nigrescens, M. oedocephali, M. megachiliensis*), *Yarrowia lipolytica, Aureobasidium* sp., *Trichosporonoides* sp., *Trigonopsis variabilis, Trichosporon* sp., *Moniliellaacetoabutans* sp., *Typhula variabilis, Candida magnoliae, Ustilaginomycetes* sp., *Pseudozyma tsukubaensis*, yeast species of genera *Zygosaccharomyces, Debaryomyces, Hansenula* and *Pichia*, and fungi of the dematioid genus *Torula* (e.g., *T. corallina*).

Many such microbial strains are publicly available, either commercially or through depositories such as the ATCC (American Type Culture Collection, Manassas, Va., USA), the NRRL (Agricultural Research Service Culture Collection, Peoria, Ill., USA), or the DSMZ (Deutsche Sammlung von Mikroorganismen and Zellkulturen GmbH, Braunschweig, Germany), to name a few.

According to some embodiments, the microorganism used for fermentation may include a yeast. Commercially available yeasts include, for example, ETHANOL RED® (available from Lesaffre Advanced Fermentations, USA), FALK®(available from AB Biotek), SUPERSTART™ (available from Lallemand Biofuels & Distilled Spirits, USA), GERT STRAND® (available from Gert Strand AB, Sweden) and FERMOL® (available from DSM Specialties).

In accordance with various embodiments, microorganisms that are suitable to saccharify the biomass material and produce sugars may also be used in the fermentation process for the purposes of converting those sugars into useful products.

EXAMPLES

The systems and methods described herein will be further illustrated through the following examples, which are illustrative in nature and are not intended to limit the scope of the disclosure.

Example Aeration Blower System

An example of a blower system suitable for use in the fermentation processes and systems discussed herein includes two SPENCER® POWER MIZER® Series 2500 blowers, Model Number CS21R96, available from Spencer Turbine Co. (Windsor, CT). Each of the blowers is rated 650 ICFM at 11 psig and include a six inch flanged inlet and a five inch flanged outlet. Each blower is powered by a 50 HP, 460 Volt, three-phase, 60 Hz, 3600 rpm, TEFC motor.

The blower system also includes a common water-cooled heat exchanger (HEX) with 304 SS housing, 304L SS casing, 304 SS (8 inch) flanged air inlet and outlet, and 1.5 inch copper flanges for the water supply lines. An example of the water-cooled heat exchanger includes the C-Series, Model Number C-125 available from Xchanger, Inc. (Hopkins, Minn.). The heat exchanger is a fin-tube assembly constructed from copper tubes and aluminum fins. The performance metrics for this heat exchanger are outlined below in Table 1:

TABLE 1

Performance Metrics of HEX

| | Process Media Side | Service Media Side |
| --- | --- | --- |
| Fluid Circulated | Air | Water |
| Volumetric Flow Rate | 1,100.0 Std. ft$^3$/min. | 42.9 gal/min. |
| Total Fluid Entering | 4,933.5 lb/hr | 21,401.9 lb/hr |
| Liquid | | 21,401.9 lb/hr |
| Water Vapor | 27.4 lb/hr | |
| Non-Condensibles Vaporized or (Cond.) | 4,906.1 lb/hr | |
| Temperature In | 266.0° F. | 60.0° F. |
| Temperature Out | 86.0° F. | 70.0° F. |
| Inlet Pressure (Absolute) | 25.696 lb/in$^2$ | |
| Velocity (Standard) | 1,013.8 ft/min | 5.0 ft/sec |
| Pressure Loss | 0.11 lb/in$^2$ | 2.0 lb/in$^2$ |
| Fouling Factor | 0.00010 ft$^2$-° F.-hr/BTU | 0.00100 ft$^2$-° F.-hr/BTU |

Total Heat Exchanged: 214,284 BTU/hr

In addition, the heat exchanger has a design temperature and pressure of 300° F. and 12.0 lb/in$^2$ for the process media side and 200° F. and 100.0 lb/in$^2$ for the service media side, respectively.

One or more valves are also included in the blower system, including modulating (6 inch) valves (e.g., 4-20 mA), butterfly valves (6 inch), check valves (6 inch), a water solenoid valve for the heat exchanger, and a temperature control valve to maintain the heat exchanger discharge temperature. Also included are five inch flanges with six inch flange companion adapters, and six inch flanged expansion joints. A six inch inlet silencer/filter assembly is also included for use with the blower.

The blower system also includes one or more sensors and other measuring or process feedback devices. For example, the system includes at least one RTD (Resistance Temperature Detector) sensor and transmitter for inboard and outboard blower bearings, as well as for the inlets and outlets of the heat exchanger. The inboard and outboard lower bearings also include vibration sensors and transmitters. An RTD device and a pressure sensor are also used to measure the temperature and pressure of the common discharge. One or more flow meters are also used to measure the air flow rates.

A common EMBC anti-surge system is also used in combination with the blower system, and includes a motor actuated air-bleed valve, NEMA 4 actuator, and an inline TEE air silencer fitted with a protective screen.

A NEMA 12 control panel is also included with the system.

The fermentation system described herein may be used for cellulose enzyme production and has a production rate of approximately 1 g/L per day.

In accordance with the system described above, a cellulase fermentation was run with the media volume of approximately 1,600 gal. The major components of the fermentation media were corn cob, rice bran, and ammonium sulfate where corn cob was the main inductant. The fermentation was inoculated with 5% (V/V) of seed inoculum, and the reactor was sparged with air at ~64 sCFM (~0.3 VVM) while agitated at ~63 RPM for 10 days. The pH was kept above 3.8, and the temperature was at 27±3° C. for the entire run. The titer of the product was approximately 11 g/L.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

The invention claimed is:

1. A system for delivering air to an aqueous liquid for aerobic fermentation of the aqueous liquid, comprising:
    a vessel having a length to diameter ratio of less than 2:1 and a volume of at least 10,000 gallons;
    an aeration system that maintains a dissolved oxygen concentration of at least 10% in the aqueous liquid, the aeration system including at least one sparge tube having a pore size of less than 5 microns and a porosity of greater than 50 percent in fluid communication with an interior of the vessel;
    at least one blower configured to deliver air at a pressure of less than 15 psig to the at least one sparge tube; and
    a heat exchanger in fluid communication between the at least one blower and the at least one sparge tube that cools the air to below 100° F. (37.8° C.) prior to entering the at least one sparge tube.

2. The system of claim 1, wherein the at least one sparge tube is constructed from a sintered, porous metal.

3. The system of claim 1, wherein a distance from the at least one sparge tube to a top surface of the aqueous liquid is not more than 40 feet.

4. The system of claim 1, wherein the at least one sparge tube is positioned in a lower portion of the vessel.

5. The system of claim 4, wherein the at least one sparge tube is mounted to a sidewall of the vessel.

6. The system of claim 1, further comprising at least one filter configured to filter air delivered from the at least one blower to the at least one sparge tube.

7. The system of claim 6, wherein the heat exchanger has an inlet in fluid communication with an outlet of the blower and an outlet in fluid communication with the at least one filter.

8. The system of claim 7, further comprising flexible conduit material coupled to the at least one filter and the heat exchanger.

9. The system of claim 6, wherein the system includes a plurality of sparge tubes and a plurality of filters positioned at equidistant positions around a perimeter of the vessel such that each sparge tube of the plurality of sparge tubes is paired with a filter of the plurality of filters.

10. The system of claim 9, wherein the plurality of sparge tubes and the plurality of filters connect at a positions external to the vessel.

11. The system of claim 1, further comprising at least one condenser in communication with an interior of the vessel and configured to condense sparge bubbles.

12. The system of claim 11, wherein the at least one condenser is positioned at a top of the vessel.

13. The system of claim 12, further comprising an outlet filtration assembly in fluid communication with the at least one condenser.

14. The system of claim 1, further comprising a mixing system positioned within the interior of the vessel.

15. The system of claim 14, wherein the mixing system includes a top impeller configured to generate a lowering force and a bottom impeller configured to generate a lifting force within the aqueous liquid.

16. A system for providing air to a fermentation process, comprising:
    a fermentation broth disposed in a vessel having a length to diameter ratio of less than 2:1 and a volume of at least 10,000 gallons;
    an aeration system that maintains a dissolved oxygen concentration of at least 10% in the fermentation broth, the aeration system including a sparge tube in fluid communication with the fermentation broth and having a pore size of less than 5 microns and a porosity of greater than 50 percent;
    at least one blower in fluid communication with the fermentation broth, the at least one blower configured to deliver air at a pressure of less than 15 psig into the vessel through the sparge tube for aerobic fermentation of the fermentation broth; and
    a heat exchanger in fluid communication between the at least one blower and the sparge tube that cools the air to below 100° F. (37.8° C.) prior to entering the sparge tube.

17. The system of claim 16, wherein the at least one blower includes a driver motor equipped with a rotor.

18. The system of claim 16, wherein the pore size is 1 micron or less.

* * * * *

UNITED STATES PATENT AND TRADEMARK OFFICE
CERTIFICATE OF CORRECTION

PATENT NO. : 10,364,412 B2
APPLICATION NO. : 15/112909
DATED : July 30, 2019
INVENTOR(S) : Marshall Medoff et al.

It is certified that error appears in the above-identified patent and that said Letters Patent is hereby corrected as shown below:

In the Specification

Column 6, Line 15, delete "sandwichinHg" and insert -- sandwiching --.

Column 17, Line 17, delete "*pollens*" and insert -- *pollinis* --.

Column 17, Line 31, delete "and" and insert -- und --.

Signed and Sealed this
Tenth Day of September, 2019

Andrei Iancu
*Director of the United States Patent and Trademark Office*